US012662700B2

(12) United States Patent
Tong et al.

(10) Patent No.: US 12,662,700 B2
(45) Date of Patent: Jun. 23, 2026

(54) METHODS AND DEVICES FOR MEASURING DUPLEX UNWINDING OR STRAND EXCHANGE EFFICIENCY

(71) Applicant: REVVITY HEALTH SCIENCES, INC., Waltham, MA (US)

(72) Inventors: Yanhong Tong, Boxford, MA (US); Yali Sun, Melrose, MA (US); Thomas Perroud, Lexington, MA (US)

(73) Assignee: REVVITY HEALTH SCIENCES, INC, Waltham, MA (US)

( * ) Notice: Subject to any disclaimer, the term of this patent is extended or adjusted under 35 U.S.C. 154(b) by 112 days.

(21) Appl. No.: 17/863,110

(22) Filed: Jul. 12, 2022

(65) Prior Publication Data

US 2024/0018578 A1     Jan. 18, 2024

(51) Int. Cl.
    *C12Q 1/6853*        (2018.01)
    *G01N 21/64*         (2006.01)

(52) U.S. Cl.
    CPC ....... *C12Q 1/6853* (2013.01); *G01N 21/6428* (2013.01); *G01N 2021/6439* (2013.01)

(58) Field of Classification Search
    None
    See application file for complete search history.

(56) References Cited

U.S. PATENT DOCUMENTS

| | | | |
|---|---|---|---|
| 5,948,227 | A | 9/1999 | Dubrow |
| 5,976,336 | A | 11/1999 | Dubrow et al. |
| 6,042,710 | A | 3/2000 | Dubrow |
| 6,440,284 | B1 | 8/2002 | Dubrow |
| 7,081,190 | B2 | 7/2006 | Dubrow |
| 7,276,330 | B2 | 10/2007 | Chow et al. |
| 7,282,328 | B2 | 10/2007 | Kong et al. |
| 7,419,784 | B2 | 9/2008 | Dubrow et al. |
| 7,662,594 | B2 | 2/2010 | Kong et al. |
| 7,666,598 | B2 | 2/2010 | Piepenburg et al. |
| 8,637,250 | B2 | 1/2014 | Jenison |
| 2018/0363041 | A1 | 12/2018 | Maar |
| 2021/0403979 | A1 | 12/2021 | Ellington et al. |

OTHER PUBLICATIONS

Andresen et al. Helicase dependent OnChip-amplification and its use in multiplex pathogen detection. Clinica Chimica Acta 403:244-248 (2009). (Year: 2009).*
An et al. Characterization of a Thermostable UvrD Helicase and Its Participation in Helicase-dependent Amplification. The Journal of Biological Chemistry 280:28952-28958 (2005). (Year: 2005).*
Schoske et al. Multiplex PCR design strategy used for the simultaneous amplification of 10 Y chromosome short tandem repeat (STR) loci. Anal. Bioanal. Chem. 375:333-343 (2003). (Year: 2003).*
Doseeva et al. Multiplex isothermal helicase-dependent amplification assay for detection of Chlamydia trachomatis and Neisseria gonorrhoeae. Diagnostic Microbiology and Infectious Disease 71:354-365 (2011). (Year: 2011).*

(Continued)

*Primary Examiner* — Samuel C Woolwine
(74) *Attorney, Agent, or Firm* — Fish & Richardson P.C.

(57)                ABSTRACT

Provided herein are quantitative assays to evaluate duplex unwinding efficiency or strand exchange efficiency during isothermal amplification.

28 Claims, 10 Drawing Sheets

Specification includes a Sequence Listing.

(56) References Cited

OTHER PUBLICATIONS

Belon et al., "Monitoring helicase activity with molecular beacons," BioTechniques, Oct. 2008. 45(4):433-42.

Earnshaw, "Evaluation of FlashPlate in a Helicase Assay," Perkin Elmer, available no later than Jul. 11, 2022, retrieved on Aug. 22, 2023, retrieved from URL < https://resources.perkinelmer.com/corporate/cmsresources/images/44-73838fsp_file5evalinhelicaseassay.pdf>, 4 pages.

FDA.gov [online], "In Vitro Diagnostics EUAs—Molecular Diagnostic Tests for SARS-CoV-2," available on or before Mar. 26, 2021, via Internet Archive: Wayback Machine URL<http://web.archive.org/web/20210326223647/https://www.fda.gov/medical-devices/coronavirus-disease-2019-covid-19-emergency-use-authorizations-medical-devices/in-vitro-diagnostics-euas-molecular-diagnostic-tests-sars-cov-2>, retrieved on Aug. 22, 2023, URL<https://www.fda.gov/medical-devices/covid-19-emergency-use-authorizations-medical-devices/in-vitro-diagnostics-euas-molecular-diagnostic-tests-sars-cov-2>, 27 pages.

George et al., "A Homogeneous Imaging Assay for DNA Helicase Activity using a Quenched DNA Duplex Substrate," Perkin Elmer, available no later than Jul. 11, 2022, retrieved on Aug. 22, 2023, retrieved from URL <https://resources.perkinelmer.com/corporate/cmsresources/images/44-73762pst_008908_36pstahomogeneousimagingassayactivity.pdf>.

International Search Report and Written Opinion in International Appln. No. PCT/US2023/070032, mailed on Nov. 6, 2023, 14 pages.

Lixin et al., "Characterization of a thermostable UvrD helicase and its participation in helicase-dependent amplification," Journal of Biological Chemistry, Jun. 13, 2005, 280(32):28952-8.

Lucius et al., Fluorescence Stopped-flow Studies of Single Turnover Kinetics of _E. coli_ RecBCD Helicase-catalyzed DNA Unwinding, Journal of Molecular Biology, Jun. 11, 2004, 339(4):731-50 (abstract only).

Mendoza et al., "A fluorescence-based helicase assay: application to the screening of G-quadruplex ligands," Nucleic Acids Research, Mar. 12, 2015, 43(11):e71.

Obande et al., "Current and Future Perspectives on Isothermal Nucleic Acid Amplification Technologies for Diagnosing Infections," Infection and Drug Resistance, Feb. 12, 2020, 13:455-83.

Putnam et al., "Resonant and localized breathing modes in terminal regions of the DNA double helix," Biophysics Journal, Aug. 1981, 35(2):271-87.

Roychoudhury et al., "Influence of nucleotide sequence adjacent to duplex DNA termini on 3' terminal labeling by terminal transferase," Nucleic Acids Research, Apr. 1979, 6(4):1323-33.

Twistdx.co [online] "Using PCR primers with standard Recombinase Polymerase Amplification reagents," available on or before Jan. 21, 2022, via Internet Archive: Wayback Machine URL<http://web.archive.org/web/20220121114428/https://www.twistdx.co.uk/rpa/using-pcr-primers/>, retrieved on Aug. 22, 2023, URL<https://www.twistdx.co.uk/rpa/using-pcr-primers/>, 3 pages.

Zeng et al., "SARS-CoV-2 helicase NSP13 hijacks the host protein EWSR1 to promote viral replication by enhancing RNA unwinding activity," Infectious Medicine, Mar. 2022, 1(1):7-16.

\* cited by examiner

| Condition | Primer:Duplex Ratio | Isothermal Amplification Mix (with unwinding activities) | Polymerase + Buffer Mix (without unwinding activities) |
|---|---|---|---|
| 1 | 0:1 | 100% | 100% |
| 2 | 1:1 | 100% | 50% |
| 3 | 4:1 | 100% | 20% |

Aligning

No Enzyme Control

Isothermal Amplification mix

Polymerase + Buffer only

Size(nt)

Marker          Primers

Extended products (shorter fragment)

Pre-annealed duplex (longer fragment)

| Condition | Primer:Duplex Ratio | Isothermal Amplification Mix (with unwinding activities) | Polymerase + Buffer Mix (without unwinding activities) |
|---|---|---|---|
| 1 | 1:1 | 50% | 0% |
| 2 | 2:1 | 67% | 0% |

SEQUENCE LISTING

```
Sequence total quantity: 5
SEQ ID NO: 1              moltype = DNA  length = 80
FEATURE                   Location/Qualifiers
source                    1..80
                          mol_type = other DNA
                          organism = synthetic construct
SEQUENCE: 1
cacaatcaaa tgacacagac tgtgtgtagt gtgaaagtta atcgaactgt tggaatctgc   60
acgttcagca tagcttgcat                                                80

SEQ ID NO: 2              moltype = DNA  length = 110
FEATURE                   Location/Qualifiers
source                    1..110
                          mol_type = other DNA
                          organism = synthetic construct
SEQUENCE: 2
cacaatcaaa tgacacagac tgtgtgtagt gtgaaagtta atcgaactgt tggaatctgc   60
acgttcagca tagcttgcat acaagagcgc tcatgagaca ataacactga             110

SEQ ID NO: 3              moltype = DNA  length = 20
FEATURE                   Location/Qualifiers
source                    1..20
                          mol_type = other DNA
                          organism = synthetic construct
SEQUENCE: 3
atgcaagcta tgctgaacgt                                                20

SEQ ID NO: 4              moltype = DNA  length = 35
FEATURE                   Location/Qualifiers
source                    1..35
                          mol_type = other DNA
                          organism = synthetic construct
```

-continued

```
SEQUENCE: 4
atgcaagcta tgctgaacgt gcagattcca acagt                          35

SEQ ID NO: 5           moltype = DNA  length = 20
FEATURE                Location/Qualifiers
source                 1..20
                       mol_type = other DNA
                       organism = synthetic construct
SEQUENCE: 5
tcagtgttat tgtctcatga                                           20
```

1

METHODS AND DEVICES FOR MEASURING DUPLEX UNWINDING OR STRAND EXCHANGE EFFICIENCY

INCORPORATION BY REFERENCE

This application contains a Sequence Listing that has been submitted electronically as an XML file named "25947-0066001_SL_ST26.XML." The XML file, created on Aug. 25, 2025, is 5,419 bytes in size. The material in the XML file is hereby incorporated by reference in its entirety.

BACKGROUND

Nucleic Acid Amplification Testing (NAAT) is highly sensitive and essential for the detection of pathogens that pose one of the major threats to worldwide public health. However, most of the current NAAT assays are PCR-based assays that require instrumentation not compatible with resource-limited settings. As an alternative method to PCR-based assays, isothermal amplification-based assays are easy-to-operate processes that rapidly amplify the nucleic acids at a constant temperature, which is suitable for point-of-care settings or at-home testing. These methods have been well-accepted for clinical applications during the SARS-CoV-2 pandemic with several Emergency Use Authorization (EUA) kits approved by the FDA.

SUMMARY

The present disclosure is based, at least in part, on the development of quantitative assays that utilize fragment analysis to evaluate duplex unwinding efficiency or strand exchange efficiency during isothermal amplification.

Isothermal technologies are based on a group of synergistic enzymes, such as HDA (helicase-dependent amplification) and RPA (recombinase polymerase amplification), that open the DNA duplex without thermocycling. In HDA and RPA technologies, rapid isothermal amplification depends on the synchronization of multiple events (duplex unwinding, primer binding, polymerase extension) with multiple enzymes (enzymes for duplex unwinding or strand exchange, polymerases, and accessory proteins). It is of interest to develop new assays for quantitatively analyzing duplex unwinding or strand exchange efficiency to further implement and improve isothermal amplification-based assays. Described herein are such methods and assays.

Accordingly, aspects of the present disclosure provide a method for detecting unwinding or strand exchange of a double stranded nucleic acid, the method comprising providing a sample comprising a pre-annealed duplex, wherein the pre-annealed duplex comprises a target nucleic acid and a synthetic nucleic acid comprising an optional first detectable label; a primer comprising a second detectable label; an amplifying enzyme for amplifying nucleic acids; and an unwinding enzyme for unwinding or strand exchange double stranded nucleic acids; incubating the sample under an isothermal amplification condition and for a time sufficient for nucleic acid amplification; and detecting the second detectable label and, optionally, the first detectable label, if present.

In some embodiments, the synthetic nucleic acid comprises an initial primer, and wherein the initial primer comprises the first detectable label.

In some embodiments, incubating further comprises extending the initial primer, thereby providing an extension product comprising the first detectable label; unwinding the extension product; annealing the primer comprising the second detectable label to a portion of the target nucleic acid; and extending the primer, thereby providing a further extension product comprising the second detectable label.

In some embodiments, the synthetic nucleic acid comprises an extension product of an initial primer, and wherein the initial primer comprises the first detectable label. In some embodiments, the synthetic nucleic acid comprises an elongated nucleic acid comprising about 20 or more nucleotides. In some embodiments, the elongated nucleic acid comprises the first detectable label.

In some embodiments, incubating further comprises unwinding the duplex; annealing the primer comprising the second detectable label to a portion of the target nucleic acid; and extending the primer, thereby providing a further extension product comprising the second detectable label.

In some embodiments, the method further comprises, prior to said providing, annealing the target nucleic acid and the synthetic nucleic acid, thereby forming the pre-annealed duplex; and optionally cooling the pre-annealed duplex.

In some embodiments, the method further comprises, prior to said providing, annealing the target nucleic acid and the synthetic nucleic acid, wherein the synthetic nucleic acid is configured to be an initial primer; and extending the initial primer under a polymerase primer extension condition, thereby forming the pre-annealed duplex.

In some embodiments, the method further comprises, after said incubating, inactivating the sample using thermal inactivation (e.g., about 45-100° C.) and/or chemical inactivation (e.g., chelator such as ethylenediaminetetraacetic acid (EDTA), protease such as Proteinase K, etc.).

In some embodiments, the method further comprises, prior to said detecting, purifying the sample to remove one or more chemical or biological components.

In some embodiments, the synthetic nucleic acid and the primer comprises the same nucleic acid sequence. In some embodiments, the synthetic nucleic acid is shorter than or the same length as the primer. In some embodiments, the synthetic nucleic acid is longer than the primer. In some embodiments, the synthetic nucleic acid and the primer has, independently, a length of about 5 to 100 nucleotides.

In some embodiments, the pre-annealed duplex comprises a 3'-tailed end and/or a 5'-tailed end. In some embodiments, the pre-annealed duplex comprises at least one blunt end. In some embodiments, the pre-annealed duplex has a length of about 15 to 500 base pairs.

In some embodiments, a ratio of the primer to the pre-annealed duplex is from 1:1 to 50:1.

In some embodiments, the first and second detectable labels are same or different. In some embodiments, the first and second detectable labels are, independently, provided at a 5'-end or internally.

In some embodiments, the synthetic nucleic acid comprises a plurality of first detectable labels, and/or wherein the primer comprises a plurality of second detectable labels. In some embodiments, the first and second detectable labels are selected from the group consisting of a fluorescent label, a radioactive label, a chemiluminescent label, or a dye.

In some embodiments, the sample further comprises 3'-amino-2',3'-dideoxyribonucleotide 5'-triphosphates (nNTPs), a divalent ion, a denaturant, a buffer, and/or a salt.

In some embodiments, the amplifying enzyme and/or the unwinding enzyme is selected from the group consisting of a helicase, a recombinase, a polymerase, a reverse transcriptase, a thermophilic form thereof, a thermostable form thereof, and a recombinant form thereof.

In some embodiments, the isothermal amplification condition comprises a temperature of about 20 to 75° C.

In some embodiments, detecting comprises electrophoresis analysis, optionally on a microfluidic device. In some embodiments, the electrophoresis analysis comprises analysis of fragment size of an amplicon comprising the second detectable label. In some embodiments, the electrophoresis analysis further comprises comparing the fragment size of the amplicon to a labeled size standard (e.g., a fluorescently-labeled size standard).

Aspects of the present disclosure provide a kit comprising a pre-annealed duplex, a primer comprising a second detectable label, an amplifying enzyme, an unwinding enzyme, and instructions for performing a method described herein.

BRIEF DESCRIPTION OF THE DRAWINGS

FIG. 1A is a non-limiting schematic diagram showing reaction mixtures for detecting duplex unwinding during isothermal amplification.

FIG. 2A is a non-limiting schematic diagram showing reaction mixtures for detecting duplex unwinding during isothermal amplification. FIG. 2B is a non-limiting schematic diagram of an electropherogram showing analysis of fluorescence fragments produced in the reaction mixtures. FIG. 2C is a chart showing theoretical percentages of extension products for reaction mixtures with different primer:duplex ratios. FIG. 2D is a non-limiting schematic diagram showing different pre-annealed duplexes that can be used in methods described herein.

DETAILED DESCRIPTION

Provided herein are methods for detecting unwinding or strand exchange of double stranded nucleic acid. Such methods can employ a labeled nucleic acid in a pre-annealed duplex and/or in a primer. By using such labeled nucleic acids, unwinding and extension events can be monitored during isothermal amplification. For instance, unwinding can be detected by using a pre-annealed duplex including (i) a target strand (or template) bound to (ii) a synthetic nucleic acid that is labeled with a detectable label. Unwinding would release the synthetic nucleic acid, and this nucleic acid (or an extension product including this nucleic acid) could be detected by way of the label.

Furthermore, unwinding would release the target strand to allow for further binding by additional primers. If the additional primers included a detectable label, then extension products of such primers would also include a label that can be detected. In this way, use of a labeled pre-annealed duplex and/or a labeled primer can allow for detection of repeated unwinding, primer annealing, and primer extension events. In some instances, a primer extension event can be considered an effective duplex unwinding event for isothermal amplification. Thus, monitoring the primer extension products instead of unwound oligonucleotides can be indicative of the efficiency of duplex unwinding under isothermal amplification.

In one non-limiting instance, the method includes a labeled primer that can be added in any useful amount (e.g., in excess or not in excess) in the reaction mixture and that can be used to form a pre-annealed duplex including a target strand and the fluorescently-labeled primer. Such methods, also referred to as Design 1, are described below with reference to FIGS. 1A-1D.

Figure 1A:
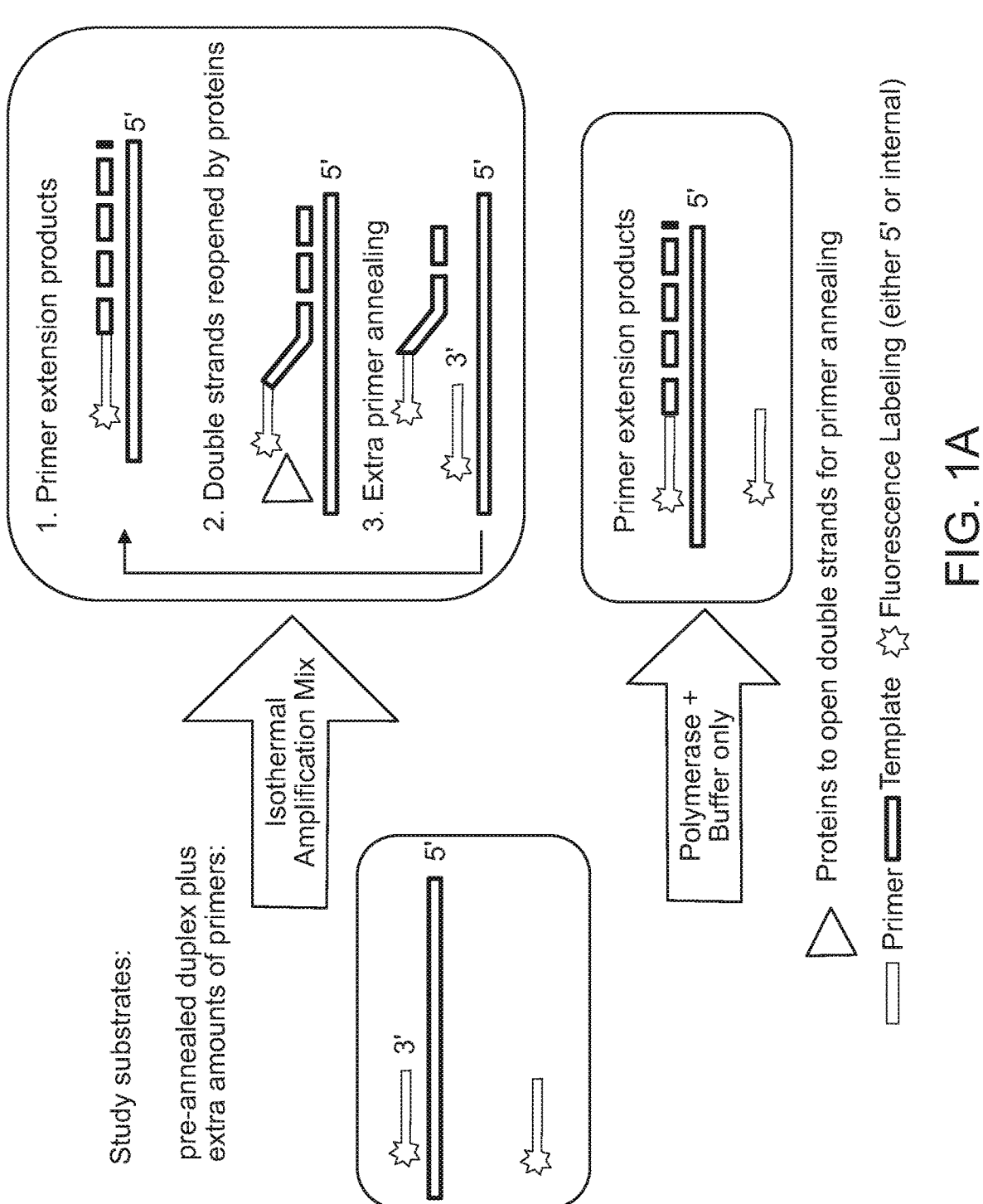
FIGS. 1A-ID are schematic diagrams illustrating a non-limiting method for detecting unwinding of double stranded nucleic acid during isothermal amplification using a fluorescently-labeled primer (Design 1). Such a method can include a fluorescently-labeled primer that is added in excess in the reaction mixture and that is used to form a pre-annealed duplex including a target strand and the fluorescently-labeled primer.

As shown in FIG. 1A (lower panel), when the reaction mixture contains a polymerase and buffer, only the fluorescently-labeled primer in the pre-annealed duplex can be extended by the polymerase. Under certain non-limiting isothermal conditions, no excess fluorescently-labeled primers in the reaction mixture are extended because limited or no unwinding of the duplex can occur to free the target strand (or template) of the duplex. Thus, the excess fluorescently-labeled primers have limited binding to the target strand, and limited levels of extension products would be formed with such excess primers.

Figure 1B:
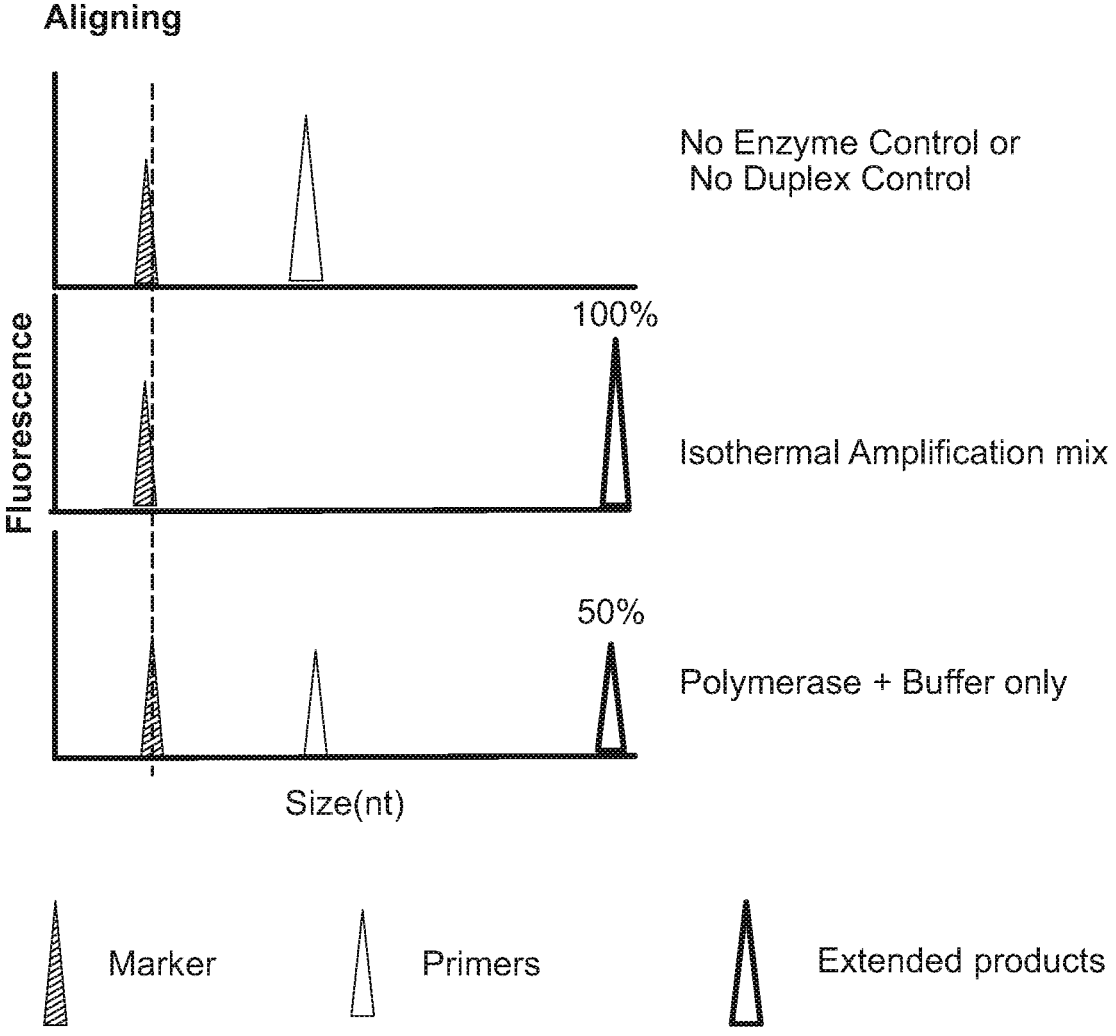
FIG. 1B is a non-limiting schematic diagram of an electropherogram showing analysis of fluorescence fragments produced in the reaction mixtures.

The amount of extension products and fluorescently-labeled primers in the reaction mixture (unextended fluorescently-labeled primers) can then be detected by size separation and fluorescence detection, e.g., using a microfluidic platform such as the LabChip® GX Touch™ Nucleic Acid Analyzer. Under polymerase-containing conditions without unwinding activity, only labeled primers in the pre-annealed duplex can be extended by the polymerase, and the detectable signal from labels within the reaction mixture would depend on the concentration of the labeled pre-annealed duplex and labeled primers in the reaction mixture. As shown in FIG. 1B, with the initial reaction mixture including a primer-to-duplex ratio of about 1:1, with polymerase only, about 50% of the detected fluorescence is from the extension products (black solid peak) and about 50% is from the fluorescently-labeled primer (gray empty peak).

As also shown in FIG. 1A (upper panel), when the reaction mixture contains an unwinding enzyme and a polymerase (isothermal amplification mix), the duplex is unwound by the unwinding enzyme, thereby freeing the target strand (or template) from the duplex to allow its binding to excess fluorescently-labeled primer in the reaction mixture. The fluorescently-labeled primer in the newly formed duplex can then be extended by the polymerase to produce fluorescently-labeled extension fragments. The amount of fluorescently-labeled extension products formed can be indicative of the duplex unwinding efficiency of the unwinding enzyme. As shown in FIG. 1B, under certain non-limiting isothermal amplification conditions, about 100% of the detected fluorescence is from the extension products (black solid peak) indicating that the unwinding enzyme efficiently unwound the duplex to allow annealing of the fluorescently-labeled primer in the reaction mixture, where it can be extended by the polymerase.

Figures 1C, 1D:
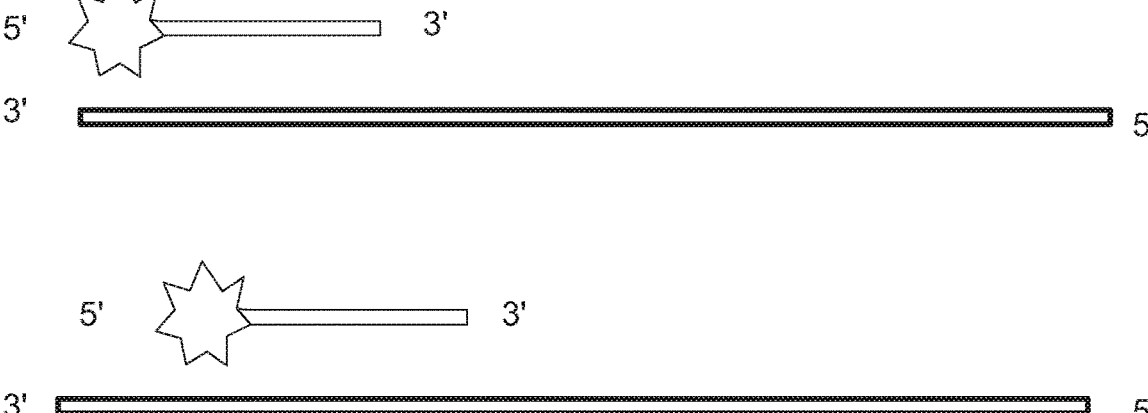
FIG. 1C is a chart showing theoretical percentages of extension products for reaction mixtures with different primer:duplex ratios.
FIG. 1D is a non-limiting schematic diagram showing different pre-annealed duplexes that can be used in methods described herein.

Theoretical percentages of extension products for reaction mixtures containing various ratios of primer to duplex are shown in FIG. 1C. When the reaction mixture contains a polymerase only, increasing the primer:duplex ratio lowers the amount of extension products formed and detected because no unwinding occurs, thereby limiting the formation of new duplexes with fluorescently-labeled primers from the reaction mixture. When the reaction mixture contains a polymerase and an unwinding enzyme, the fluorescently-labeled primers can be extended by the coordinated unwinding of the duplex by the unwinding enzyme and extension of the fluorescently-labeled primer in the newly formed duplex by the polymerase. Reaction mixtures lacking excess fluorescently-labeled primers can be used as a positive control for detection of extension products under isothermal amplification conditions.

As shown in FIG. 1D, the pre-annealed duplex can include a target nucleic acid strand that is longer than the fluorescently-labeled primer. A portion of the target nucleic acid can be sufficiently complementary to the fluorescently-labeled primer to allow for hybridization of the target nucleic acid and the fluorescently-labeled primer into a duplex. Depending on the location of the complementary portion within the target strand, the duplex can include a blunt end at one side (e.g., at a 3'-end of the target) with a 5'-tailed end; or it can include a 3'-tailed end and a 5'-tailed end. Furthermore, while fluorescent labels are shown, any detectable label can be used in such constructs or in any methods herein.

Provided herein are methods for detecting unwinding of double stranded nucleic acid using a short fluorescently-labeled primer that is added the reaction mixture and a pre-annealed duplex in which one of the strands is fluorescently-labeled. Such methods, also referred to as Design 2, are described below with reference to FIGS. 2A-2D.

Figure 2A:
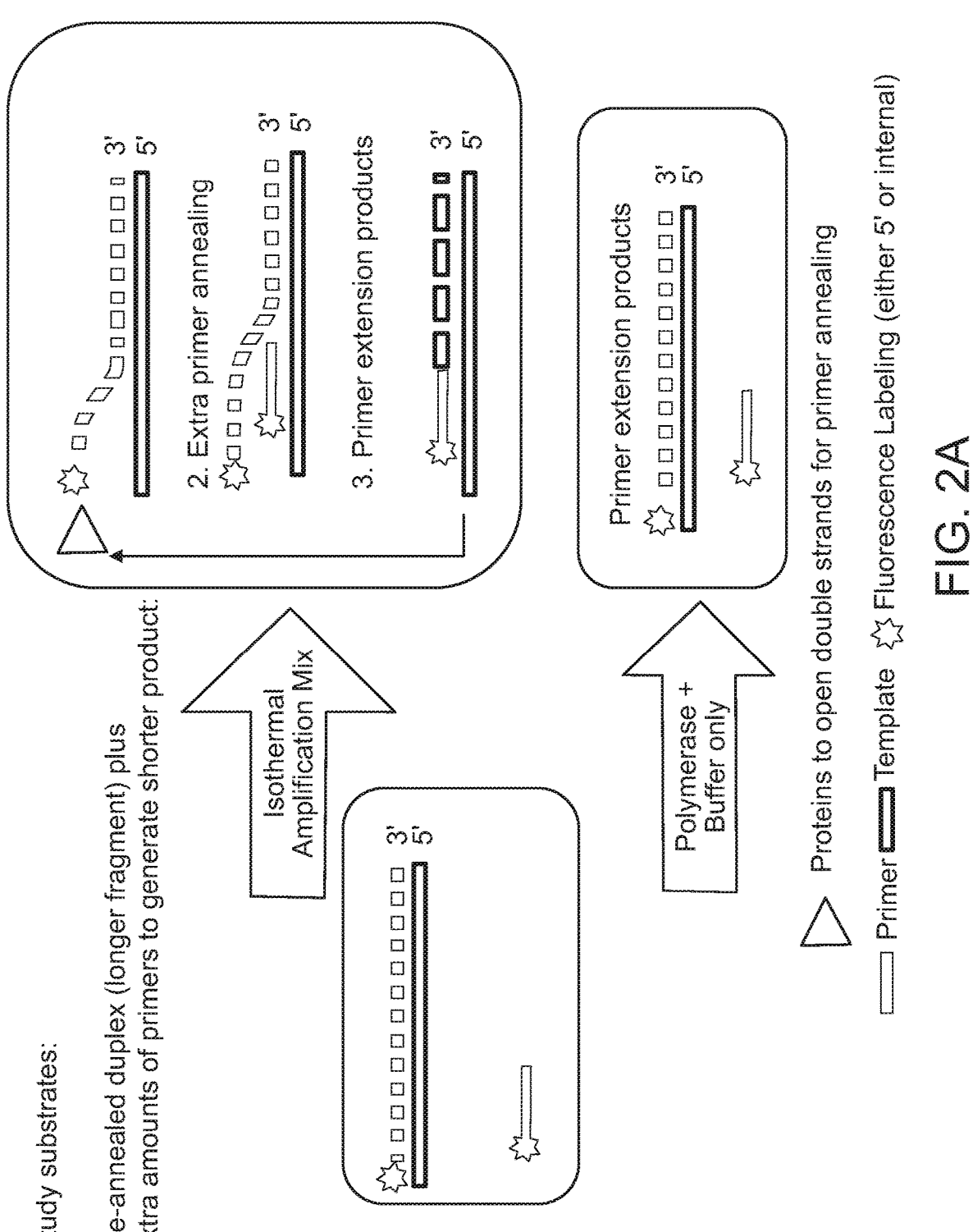
FIGS. 2A-2D are schematic diagrams illustrating another non-limiting method for detecting unwinding of double stranded nucleic acid during isothermal amplification using a fluorescently-labeled primer (Design 2). Such a method can include a fluorescently-labeled primer that is added in the reaction mixture, as well as a longer fluorescently-labeled synthetic nucleic acid that is used to form a pre-annealed duplex including a target strand and the fluorescently-labeled complementary strand.

As shown in FIG. 2A (lower panel), without proteins for duplex unwinding in the reaction mixture, fluorescently-labeled primers cannot bind to the internal sequence of the target strand, and thus only a longer fragment will be detected. By contrast, with proteins for duplex unwinding in the reaction mixture (upper panel in FIG. 2A), there will be recycling of duplex unwinding and primer binding/extension that results in the accumulation of the extended fragment, which is detected together with the longer fragment.

Figures 2B, 2C:
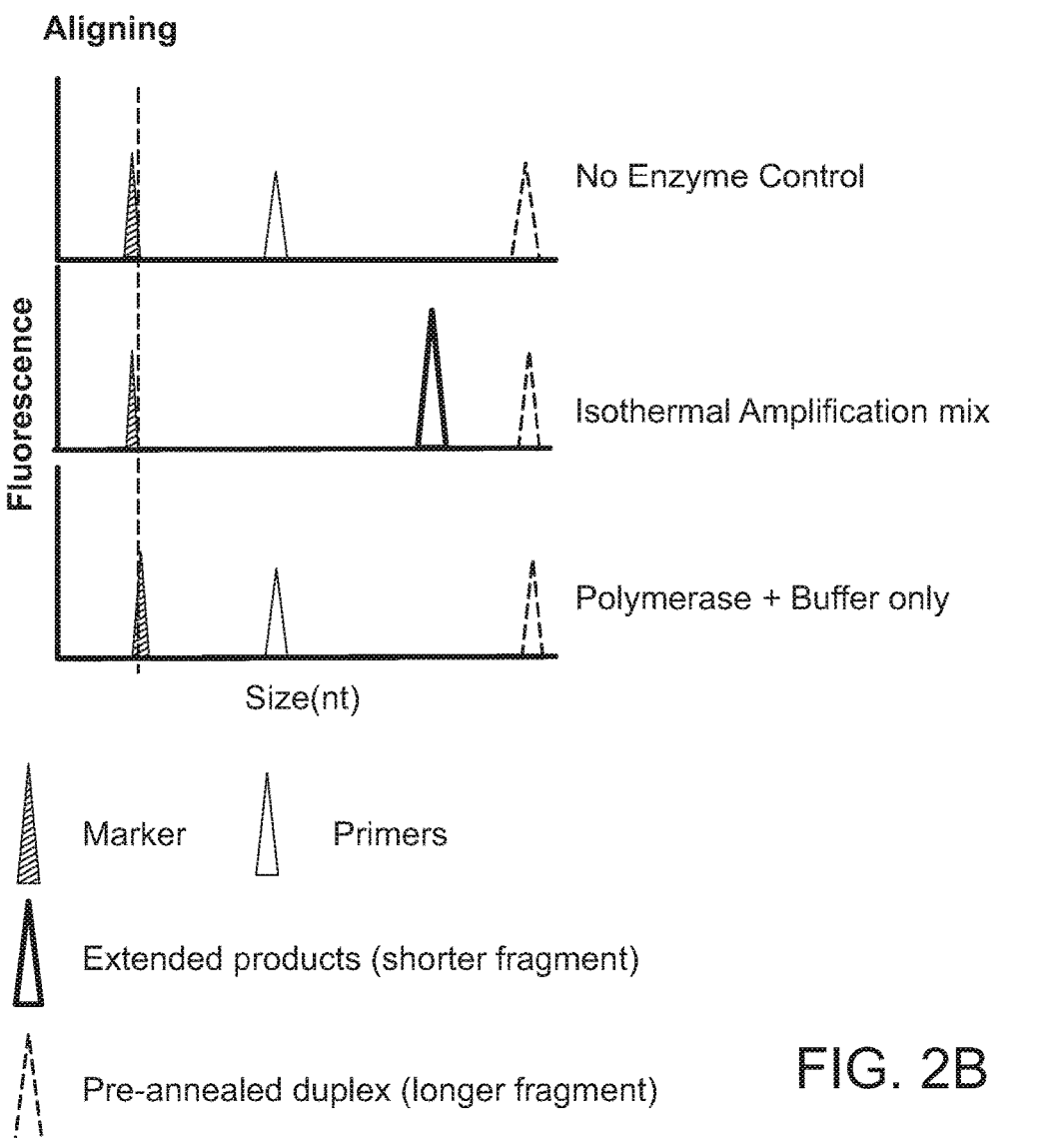

The amount of extension products and fluorescently-labeled primers in the reaction mixture (unextended fluorescently-labeled primers) can then be detected by size separation and fluorescence detection as shown in FIG. 2B. As the indicator of double-strand unwinding efficiency in isothermal amplification, the extended fragment can be analyzed in two ways: 1) a peak area ratio of the extended fragment to the initial duplex fragment (Extended-to-initial fragment ratio, shown in Example 3); and/or 2) a percentage of the extended fragment, which is calculated as the proportion of peak area of the extended fragment in total fragments including the extended fragment and the initial long fragment (shown in Example 2 and 3).

Theoretical percentages of extension products for reaction mixtures containing various ratios of primer to duplex are shown in FIG. 2C. When the primer-to-duplex ratio is 1:1, without the double-strand unwinding process, the proportion of the extended product is around 0%, whereas the initial duplex fragment accounts for 100% (or the ratio of extended-to-initial fragment is 0). With the strand unwinding process, the proportion of extended product can be around 50% (or ratio of extended-to-initial fragment is around 1) or more depending on the extra amount of primers and unwinding efficiency.

Figure 2D:
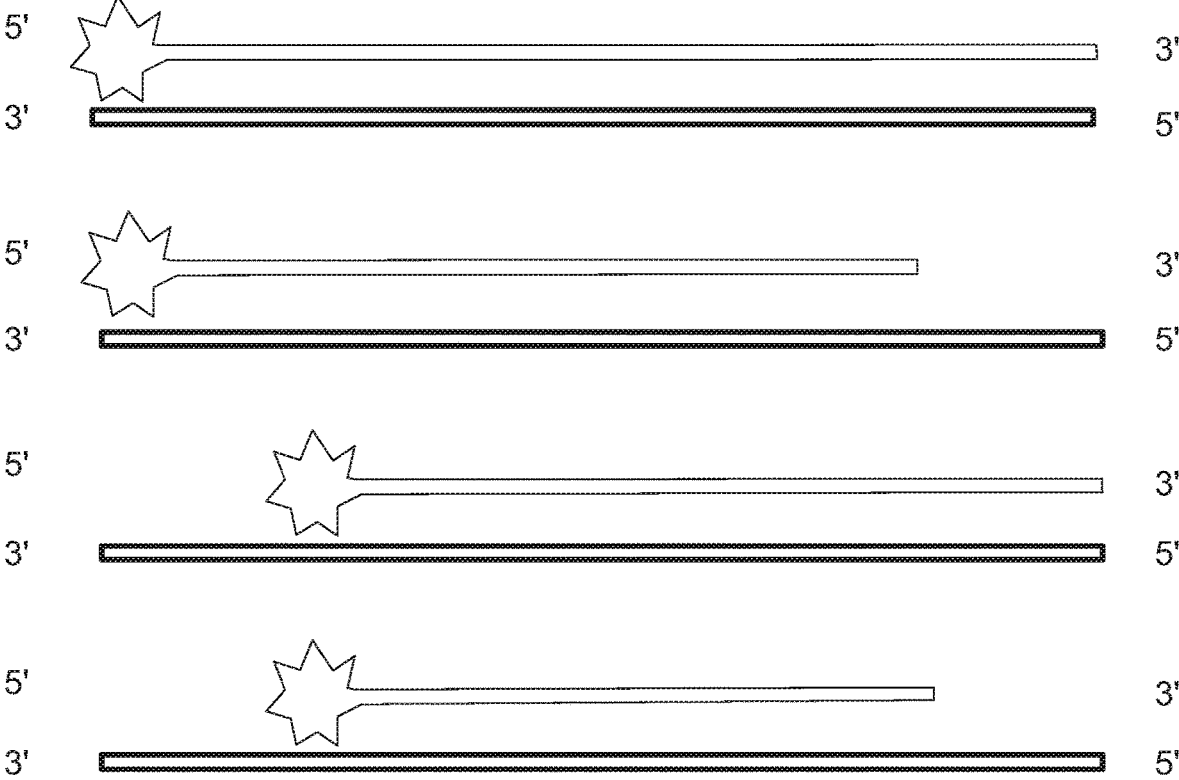

As shown in FIG. 2D, the pre-annealed duplex can include a target nucleic acid strand and a fluorescently-labeled stand. The target strand and the fluorescently-labeled strand can be about the same length; or the fluorescently-labeled strand can be shorter than the target strand. As such, the duplex can include a blunt end at one side or both sides, or it can include a 3'-tailed end and/or a 5'-tailed end. Furthermore, while fluorescent labels are shown, any detectable label can be used in such constructs or in any methods herein.

I. Components for Use in Unwinding or Strand Exchange Assays

The methods and devices disclosed herein involve: (i) a pre-annealed duplex comprising a target nucleic acid and a synthetic nucleic acid, which is optionally conjugated to a detectable label; (ii) a primer; (iii) an amplifying enzyme; and (iv) an enzyme for unwinding or strand exchange of double stranded nucleic acids. The primer, and optionally the synthetic nucleic acid, is conjugated to a detectable label.

(i) Pre-Annealed Duplexes

A pre-annealed duplex refers to a double-stranded nucleic acid formed from annealing or hybridizing a target nucleic acid and a synthetic nucleic acid, each of which is a single-stranded nucleic acid. The duplex can include at least one double-stranded region that may or may not extend along the entirety of the target nucleic acid. For example, the duplex may include one or more regions that are characterized as being single-stranded, such as at a tail end.

A target nucleic acid and a synthetic nucleic acid can be any length suitable for hybridization and formation of the duplex. The target nucleic acid and the synthetic nucleic acid can be the same length or a different length.

In some embodiments, the target nucleic acid has a length of about 15 to about 500 nucleotides, e.g., about 25 to about 500 nucleotides, about 50 to about 500 nucleotides, about 75 to about 500 nucleotides, about 100 to about 500 nucleotides, about 150 to about 500 nucleotides, about 200 to about 500 nucleotides, about 250 to about 500 nucleotides, about 300 to about 500 nucleotides, about 350 to about 500 nucleotides, about 400 to about 500 nucleotides, about 450 to about 500 nucleotides, about 15 to about 450 nucleotides, about 15 to about 400 nucleotides, about 15 to about 350 nucleotides, about 15 to about 300 nucleotides, about 15 to about 250 nucleotides, about 15 to about 200 nucleotides, about 15 to about 150 nucleotides, about 15 to about 100 nucleotides, about 15 to about 50 nucleotides, or about 15 to about 25 nucleotides.

In some embodiments, the synthetic nucleic acid has a length of about 10 to about 100 nucleotides, e.g., about 15 to about 100 nucleotides, about 20 to about 100 nucleotides, about 30 to about 100 nucleotides, about 40 to about 100 nucleotides, about 50 to about 100 nucleotides, about 60 to about 100 nucleotides, about 70 to about 100 nucleotides, about 80 to about 100 nucleotides, about 90 to about 100 nucleotides, about 10 to about 90 nucleotides, about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 10 to about 15 nucleotides.

A target nucleic acid and a synthetic nucleic acid can include any sequence, e.g., a naturally occurring sequence or a modified sequence. The target nucleic acid and the synthetic nucleic acid can be obtained from one or more sources, e.g., isolated from a biological sample or obtained from commercial sources.

All or a portion of a synthetic nucleic acid can be complementary or substantially complementary to a target nucleic acid. Substantially complementary or substantial complementarity refers to nucleotide sequences that will hybridize with each other. For example, the target nucleic acid and synthetic nucleic acid can be at least 75%, at least 80%, at least 85%, at least 90%, at least 95%, at least 96%, at least 97%, at least 98%, at least 99%, or more comple- mentary to each other over any useful region (e.g., over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions). Stringent conditions can refer to conditions under which a nucleic acid having complementarity or substantial complementarity to a target sequence predomi- nantly hybridizes with the target sequence, and substantially does not hybridize to non-target sequences. Stringent con- ditions are generally sequence-dependent, and vary depend- ing on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybrid- ization and the strategy of nucleic acid probe assay", Else- vier, N.Y.

Depending on the length and complementarity of the target nucleic acid and the synthetic nucleic acid, the pre- annealed duplex can include a 3'-tailed end, a 5'-tailed end, a blunt end, or a combination thereof. In some embodiments, the pre-annealed duplex includes one blunt end and a 3'-tailed end or a 5'-tailed end. In some embodiments, the pre-annealed duplex includes two blunt ends.

A target nucleic acid and a synthetic nucleic acid can include DNA, RNA, or a combination thereof (e.g., a DNA/RNA hybrid). A target nucleic acid and/or a synthetic nucleic acid can include one or more modified nucleotides. Any modified nucleotide known in the art can be included in the target nucleic acid and/or the synthetic nucleic acid for use in methods described herein. The one or more modified nucleotides can be include anywhere in the target nucleic acid and/or in the synthetic nucleic acid, e.g., 3' end of the nucleic acid, 5' end of the nucleic acid, internally, or a combination thereof.

A synthetic nucleic acid can include the same sequence as a primer or the synthetic nucleic acid can include a different sequence. The synthetic nucleic acid can be shorter than, longer than, or the same length as the primer. In some examples, the synthetic nucleic acid comprises a primer. In some examples, the synthetic nucleic acid comprises an extension product of a primer.

A synthetic nucleic acid can include one or more detect- able labels, e.g., detectable labels known in the art or described herein. The one or more detectable labels can be included anywhere in the synthetic nucleic acid, e.g., 3' end of the nucleic acid, 5' end of the nucleic acid, internally, or a combination thereof. In some non-limiting examples, a plurality of detectable labels may be present. In other non-limiting examples, a label is not present at the 3' end.

Pre-annealed duplexes can be formed using any method known in the art or described herein. For example, a pre-annealed duplex can be formed by mixing a target nucleic acid and a synthetic nucleic acid, heating the mixture (e.g., 95° C. for 5 minutes), and allowing the mixture to cool to room temperature (e.g., about 60 minutes). In some examples, a pre-annealed duplex can be formed by mixing a target nucleic acid and a primer, optionally an extension product of the primer, heating the mixture, and allowing the mixture to cool to room temperature.

(ii) Primers

A primer refers to an oligonucleotide that includes a nucleotide sequence capable of hybridizing or annealing to a target nucleic acid. The primer hybridizes or anneals at or near a specific region of interest (also referred to as a target sequence) in the target nucleic acid.

A primer can be any length suitable for hybridizing to a target nucleic acid. The primer can be the same length as the target nucleic acid or the primer can be shorter in length than the target nucleic acid. In some embodiments, the primer has a length of about 10 to about 100 nucleotides, e.g., about 15 to about 100 nucleotides, about 20 to about 100 nucleotides, about 30 to about 100 nucleotides, about 40 to about 100 nucleotides, about 50 to about 100 nucleotides, about 60 to about 100 nucleotides, about 70 to about 100 nucleotides, about 80 to about 100 nucleotides, about 90 to about 100 nucleotides, about 10 to about 90 nucleotides, about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides, or about 10 to about 15 nucleotides.

All or a portion of a primer can be complementary or substantially complementary to a target nucleic acid. Sub- stantially complementary refers to nucleotide sequences that will hybridize with each other. For example, the primer and the target nucleic acid can be at least 75%, at least 80%, at least 85%, at least 90%, at least 95%, at least 96%, at least 97%, at least 98%, at least 99%, or more complementary to each other over any useful region (e.g., over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions).

A primer can include any sequence, e.g., a naturally occurring sequence or a modified sequence. The primer can be obtained from one or more sources, e.g., isolated from a biological sample or obtained from commercial sources.

A primer can include DNA, RNA, or a combination thereof (e.g., a DNA/RNA hybrid). A primer can include one or more modified nucleotides. Any modified nucleotide known in the art can be included in primers for use in methods described herein. The one or more modified nucleotides can be include anywhere in the primer, e.g., 3' end of the primer, 5' end of the primer, internally, or a combination thereof.

A primer can include one or more detectable labels, e.g., detectable labels known in the art or described herein. The one or more detectable labels can be included anywhere in the primer, e.g., 3' end of the primer, 5' end of the primer, internally, or a combination thereof.

(iii) Amplifying Enzymes

Amplifying enzymes refers to any enzyme that synthesizes polymers of nucleic acids. Amplifying enzymes include, but are not limited to, polymerases (e.g., DNA polymerases, RNA polymerases). DNA polymerases include, but are not limited to, DNA-dependent DNA polymerases and RNA-dependent DNA polymerases including reverse transcriptases. RNA polymerases include, but are not limited to, DNA-dependent RNA polymerases and RNA-dependent RNA polymerases. Amplifying enzymes for use in methods described herein can be naturally occurring or genetically modified.

(iv) Unwinding Enzymes

Unwinding enzymes refer to any enzyme that unwinds and/or separates two nucleic acid strands (e.g., DNA, RNA, RNA-DNA hybrid). Unwinding enzymes include enzymes having unwinding and/or strand exchange activities. Examples of unwinding enzymes include, but are not limited to, helicases (e.g., DNA helicases, RNA helicases), polymerases having strand displacement activity (e.g., phi29, Bst DNA Polymerase, BcaBEST DNA polymerase, Vent (exo-) DNA polymerase, MS-2 phage DNA polymerase, z-Taq DNA polymerase, Taq polymerase, Bsm DNA polymerase (Bsm), as well as variants thereof, such as Bst 2.0 or Bst 2.0 WarmStart™ DNA polymerases (New England Biolabs, Ipswich, Mass.) and combinations thereof (e.g., a blend of a strand displacement polymerase and Taq)), recombinases (e.g., Cre recombinases, Hin recombinases, Tre recombinases, FLP recombinases), and accessory proteins for unwinding (e.g., uvsY, a recombinase loading factor). An unwinding enzyme for use in methods described herein can be a naturally occurring form or a thermophilic form thereof, thermostable form thereof, or recombinant form thereof.

(v) Detectable Labels

The primer, and optionally the synthetic nucleic acid, for use in methods and devices described herein is conjugated to a detectable label. When both the primer and the synthetic nucleic acid are conjugated to a detectable label, the detectable label can be the same or different.

As used herein, a "detectable label" refers to any molecule that is capable of releasing a detectable signal, either directly or in directly. In some embodiments, the detectable label can be a fluorophore (e.g., CY5). As used herein, the term "fluorophore" (also referred to as "fluorescent label" or "fluorescent dye") refers to moieties that absorb light energy at a defined excitation wavelength and emit light energy at a different wavelength.

Examples of fluorophores include, without limitation, cyanine derivatives (e.g., cyanine, indocarbocyanine, oxacarbocyanine, thiacarbocyanine and merocyanine), xanthene derivatives (e.g., fluorescein, rhodamine, Oregon green, eosin and Texas red), naphthalene derivatives (e.g., dansyl and prodan derivatives), pyrene derivatives (e.g., cascade blue), oxadiazole derivatives (e.g., pyridyloxazole, nitrobenzoxadiazole and benzoxadiazole), oxazine derivatives (e.g., Nile red, Nile blue, cresyl violet and oxazine 70), acridine derivatives (e.g., proflavin, acridine orange and acridine yellow), arylmethine derivatives (e.g., auramine, crystal violet and malachite green), tetrapyrrole derivatives (e.g., porphin, phthalocyanine and bilirubin), coumarin derivatives, or fluorescent proteins (e.g., green fluorescent protein).

In some embodiments, the detectable label is a radioactive label (e.g., $^{35}$S, $^{125}$I, or radioactive phosphates such as $^{32}$P or $^{33}$P). In some embodiments, the detectable label is a chemiluminescent label (e.g., acridinium esters or ruthenium esters). Detectable labels include other labels such as biotin, avidin, streptavidin, digoxigenin, haptens, quantum dots, nanoparticles, and the like.

II. Assays for Detecting Unwinding or Strand Exchange Efficiency

Aspects of the present disclosure provide methods for detecting unwinding of a double stranded nucleic acid. To perform the assay method described herein, a sample comprising (i) a pre-annealed duplex comprising a target nucleic acid and a synthetic nucleic acid, which is optionally conjugated to a detectable label; (ii) a primer conjugated to a detectable label; (iii) an amplifying enzyme; and (iv) an enzyme for unwinding or strand exchange of double stranded nucleic acids is incubated under isothermal amplification conditions and for a time sufficient for nucleic acid amplification. Amplification products in the sample can be detected by size and by detection of a signal released from the detectable label.

Methods described herein encompass incubating a sample for any period of time sufficient for nucleic acid amplification. In some embodiments, the sample is incubated for about 1 to 30 minutes, e.g., about 5 to 30 minutes, about 10 to 30 minutes, about 15 to 30 minutes, about 20 to 30 minutes, about 25 to 30 minutes, about 1 to 25 minutes, about 1 to 20 minutes, about 1 to 15 minutes, about 1 to 10 minutes, about 1 to 5 minutes, or about 1 to 2 minutes.

Methods described herein encompass incubating a sample at any temperature sufficient for nucleic acid amplification. In some embodiments, the sample is incubated at a temperature of about 20 to 75° C., e.g., about 25 to 75° C., about 30 to 75° C., about 35 to 75° C., about 40 to 75° C., about 45 to 75° C., about 50 to 75° C., about 55 to 75° C., about 60 to 75° C., about 65 to 75° C., about 70 to 75° C., about 20 to 70° C., about 20 to 65° C., about 20 to 60° C., about 20 to 55° C., about 20 to 50° C., about 20 to 45° C., about 20 to 40° C., about 20 to 35° C., about 20 to 30° C., or about 20 to 25° C.

Any amount of a pre-annealed duplex suitable for nucleic acid amplification can be used in methods described herein. For example, the sample can comprise a pre-annealed duplex at a concentration of 0.1 to 10 μM. In some embodiments, the sample can comprise a pre-annealed duplex at a concentration of 0.25 to 10 μM, 0.5 to 10 μM, 1 to 10 μM, 2.5 to 10 μM, 5 to 10 μM, 7.5 to 10 μM, 0.1 to 7.5 μM, 0.1 to 5 μM, 0.1 to 2.5 μM, 0.1 to 1 μM, 0.1 to 0.5 μM, or 0.1 to 0.25 μM.

Any amount of a primer suitable for nucleic acid amplification can be used in methods described herein. For example, the sample can comprise a primer at a concentration of 0.1 to 10 μM. In some embodiments, the sample can comprise a primer at a concentration of 0.25 to 10 μM, 0.5 to 10 μM, 1 to 10 μM, 2.5 to 10 μM, 5 to 10 μM, 7.5 to 10 μM, 0.1 to 7.5 μM, 0.1 to 5 μM, 0.1 to 2.5 μM, 0.1 to 1 μM, 0.1 to 0.5 μM, or 0.1 to 0.25 μM.

Any ratio of primer to pre-annealed duplex suitable for nucleic acid amplification can be used in methods described herein. For example, the sample can comprise a ratio of primer to pre-annealed duplex of 1:1 to 50:1. In some embodiments, the sample can comprise a ratio of primer to pre-annealed duplex of 1:1 to 45:1, 1:1 to 40:1, 1:1 to 35:1, 1:1 to 30:1, 1:1 to 25:1, 1:1 to 20:1, 1:1 to 15:1, 1:1 to 10:1, 1:1 to 5:1, 1:1 to 4:1, 1:1 to 3:1, or 1:1 to 2:1.

Samples can include one or more amplifying enzymes and/or one or more enzymes for unwinding or strand exchange. Samples can include additional components including, but not limited to, deoxyribonucleotide triphosphates (dNTPs, including ATP), buffers, water, salts, divalent ions (e.g., divalent cations, such as $Mg^{++}$), detergents, denaturants, crowding agents, or combinations thereof. Additional components can include one or more of the following: betaine, dimethyl sulfoxide, ethylene glycol, glycerol, formamide, 7-deaza-2'-deoxyguanosine 5'-triphosphate, 2'-deoxyinosine 5'-triphosphate, or 1,2-propanediol.

Methods provided herein can comprise inactivating the sample prior to detection of nucleic acid amplification. The sample can be inactivated via thermal inactivation (e.g., incubating at about 45-100° C.), chemical inactivation (e.g., incubating in the presence of a chelator such as EDTA or a protease such as Proteinase K), or a combination thereof.

Methods provided herein can comprise purifying the sample prior to detection of nucleic acid amplification. The purification step can be used to remove one or more chemical components (e.g., crowding agents, high salt concentrations) and/or one or more biological components (e.g., proteins such as a serum protein, an albumin, or a globulin, including bovine serum albumin (BSA) as an example). Samples can be purified using any method known in the art or described herein. In some examples, purifying the sample includes concentrating the sample. In some examples, purifying the sample is performed using a commercially available kit (e.g., ZYMO RESEARCH ZR-96 Oligo Clean & Concentrator™ kit; cat. no. D4062).

Methods provided herein encompass detecting nucleic acid amplification, which can be achieved by detecting extension products. Various methods known in the art or described herein can be used to detect the size of the extension product and the signal produced from a detectable label on the extension product. In some embodiments, extension products can be detected using electrophoresis (e.g., capillary electrophoresis, polyacrylamide gel electrophoresis), optionally on a microfluidic device. In some embodiments, the size of the extension product is determined using a labeled size standard (e.g., a fluorescently-labeled size standard).

In one non-limiting example, fragment analysis can be performed on products obtained after isothermal amplification. Such products can include extension products, primers, pre-annealed duplexes, as well as labeled forms of one or more of these. Fragment analysis can include electrophoretic separation of sample products, detection of signals arising from detectable labels of sample products, and analysis of such signals, which can include determining fragment size and/or concentration using calibration standards (e.g., ladder or marker standards).

Examples of microfluidic devices and analyses suitable for use in methods provided here are described below and in, e.g., U.S. Pat. Nos. 5,976,336; 7,419,784; 7,276,330; 7,081, 190; 5,948,227; 6,042,710; and 6,440,284, each of which is incorporated herein by reference in its entirety.

III. Microfluidic Devices

Also provided herein are microfluidic devices for detecting unwinding or strand exchange of double stranded nucleic acid. Any of the methods described herein can be performed on a microfluidic device described herein. In one non-limiting instance, microfluidic or micro is meant having at least one dimension that is less than 1 mm. For instance, a microfluidic structure (e.g., any structure described herein)

can have a length, width, height, cross-sectional dimension, circumference, radius (e.g., external or internal radius), or diameter that is less than 1 mm.

The microfluidic device can one or more inlets configured to receive a sample (e.g., any described herein), one or more outlets, as well as regions to provide fluidic communication between the inlet(s) and outlet(s). In certain instances, fluidic communication refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

Such regions can include channels, chambers, and the like. Furthermore, a region can be configured to perform any method described herein. In one embodiment, the microfluidic device can include a channel configured to transport a sample (e.g., including a pre-annealed duplex, a primer or a labeled form thereof, an amplifying enzyme for amplifying nucleic acids, an unwinding enzyme for unwinding double stranded nucleic acids, a detectable label, an extension product or a labeled form thereof, an amplicon or a labeled form thereof, as well as combinations thereof).

The microfluidic device can include a detection region in fluidic communication with the channel, in which the detection region is configured to detect any detectable label (e.g., a first and/or second detectable label, as described herein). Such a device can be used for, e.g., fragment separation and/or fragment analysis. Isothermal amplification may or may not be employed in such a device.

Optionally, the microfluidic device can be configured to perform on-chip isothermal amplification. Such a device can include an incubation region in fluidic communication with the channel and/or the detection region. In one non-limiting embodiment, the incubation region is configured to incubate the sample under an isothermal amplification condition for a time sufficient for nucleic acid amplification. Description of amplification conditions are provided herein.

IV. Kits

The present disclosure also provides kits for detecting unwinding or strand exchange of double stranded nucleic acid. Such kits can include a pre-annealed duplex and/or a target nucleic acid and a synthetic nucleic acid for forming the pre-annealed duplex; a primer; an amplifying enzyme; and an enzyme for unwinding or strand exchange of double stranded nucleic acids. The primer, and optionally the synthetic nucleic acid, can be conjugated to a detectable label.

The kit can also include instructions for practicing any of the methods described herein. Instructions supplied in the kits of the present disclosure are typically written instructions on a label or a package insert.

The kits provided herein are in suitable packaging. Suitable packaging includes, but is not limited to, containers, bottles, vials, and flexible packaging. Kits can include additional components such as buffers and interpretive information.

The following embodiments are also encompassed by the present disclosure:

1. A method for detecting unwinding or strand exchange of a double stranded nucleic acid, the method comprising providing a sample comprising a pre-annealed duplex, wherein the pre-annealed duplex comprises a target nucleic acid and a synthetic nucleic acid comprising an optional first detectable label; a primer comprising a second detectable label; an amplifying enzyme for amplifying nucleic acids; and an unwinding enzyme for unwinding or strand exchange double stranded nucleic acids; incubating the sample under an isothermal amplification condition and for a time sufficient for nucleic acid amplification; and detecting the second detectable label and, optionally, the first detectable label, if present.

2. The method of embodiment 1, wherein the synthetic nucleic acid comprises an initial primer, and wherein the initial primer comprises the first detectable label.

3. The method of embodiment 2, wherein said incubating further comprises: extending the initial primer, thereby providing an extension product comprising the first detectable label; unwinding the extension product; annealing the primer comprising the second detectable label to a portion of the target nucleic acid; and extending the primer, thereby providing a further extension product comprising the second detectable label.

4. The method of embodiment 1, wherein the synthetic nucleic acid comprises an extension product of an initial primer, and wherein the initial primer comprises the first detectable label.

5. The method of embodiment 1, wherein the synthetic nucleic acid comprises an elongated nucleic acid comprising about 20 or more nucleotides.

6. The method of embodiment 5, wherein the elongated nucleic acid comprises the first detectable label.

7. The method of embodiments 1-6, wherein said incubating further comprises: unwinding the duplex; annealing the primer comprising the second detectable label to a portion of the target nucleic acid; and extending the primer, thereby providing a further extension product comprising the second detectable label.

8. The method of embodiments 1-7, further comprising, prior to said providing annealing the target nucleic acid and the synthetic nucleic acid, thereby forming the pre-annealed duplex; and optionally cooling the pre-annealed duplex.

9. The method of embodiments 1-7, further comprising, prior to said providing annealing the target nucleic acid and the synthetic nucleic acid, wherein the synthetic nucleic acid is configured to be an initial primer; and extending the initial primer under a polymerase primer extension condition, thereby forming the pre-annealed duplex.

10. The method of embodiments 1-9, further comprising, after said incubating: inactivating the sample using thermal inactivation (e.g., about 45-100° C.) and/or chemical inactivation (e.g., chelator such as EDTA, protease such as Proteinase K, etc.).

11. The method of embodiments 1-10, further comprising prior to said detecting: purifying the sample to remove one or more chemical or biological components.

12. The method of embodiment 1, wherein the synthetic nucleic acid and the primer comprises the same nucleic acid sequence.

13. The method of embodiment 1, wherein the synthetic nucleic acid is shorter than or the same length as the primer.

14. The method of embodiment 1, wherein the synthetic nucleic acid is longer than the primer.

15. The method of embodiment 1, wherein the synthetic nucleic acid and the primer has, independently, a length of about 5 to 100 nucleotides.

16. The method of embodiments 1-15, wherein the pre-annealed duplex comprises a 3'-tailed end and/or a 5'-tailed end.

17. The method of embodiments 1-16, wherein the pre-annealed duplex comprises at least one blunt end.

18. The method of embodiments 1-17, wherein the pre-annealed duplex has a length of about 15 to 500 base pairs.

19. The method of embodiments 1-18, wherein a ratio of the primer to the pre-annealed duplex is from 1:1 to 50:1.

20. The method of embodiments 1-19, wherein the first and second detectable labels are same or different.

21. The method of embodiment 20, wherein the first and second detectable labels are, independently, provided at a 5'-end or internally.

22. The method of embodiments 20-21, wherein the synthetic nucleic acid comprises a plurality of first detectable labels, and/or wherein the primer comprises a plurality of second detectable labels.

23. The method of embodiment 20, wherein the first and second detectable labels are selected from the group consisting of a fluorescent label, a radioactive label, a chemiluminescent label, or a dye.

24. The method of embodiments 1-23, wherein the sample further comprises 3'-amino-2',3'-dideoxyribonucleotide 5'-triphosphates (nNTPs), a divalent ion, a denaturant, a buffer, and/or a salt.

25. The method of embodiments 1-24, wherein the amplifying enzyme and/or the unwinding enzyme is selected from the group consisting of a helicase, a recombinase, a polymerase, a reverse transcriptase, a thermophilic form thereof, a thermostable form thereof, and a recombinant form thereof.

26. The methods of embodiments 1-25, wherein the isothermal amplification condition comprises a temperature of about 20 to 75° C.

27. The method of embodiments 1-26, wherein said detecting comprises electrophoresis analysis, optionally on a microfluidic device.

28. The method of embodiment 27, wherein the electrophoresis analysis comprises analysis of fragment size of an amplicon comprising the second detectable label.

29. The method of embodiment 28, wherein the electrophoresis analysis further comprises comparing the fragment size of the amplicon to a labeled size standard (e.g., a fluorescently-labeled size standard).

30. A kit comprising a pre-annealed duplex, a primer comprising a second detectable label, an amplifying enzyme, an unwinding enzyme, and instructions for performing a method of embodiments 1-29.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the invention described may be more fully understood, the following examples are set forth. The examples described in this application are offered to illustrate the methods and compositions provided herein and are not to be construed in any way as limiting their scope.

Example 1: Detecting Unwinding of a Double Stranded Nucleic Acid by a DNA Helicase Using a Fluorescently-Labeled Primer (Design 1)

This Example describes detecting unwinding of double stranded nucleic acid by a DNA helicase using a fluorescently-labeled primer that is added in excess in the reaction mixture and that is used to form a pre-annealed duplex including a target strand and the fluorescently-labeled primer (Design 1).

Helicase-dependent amplification (HDA) relies on the double-stranded DNA (dsDNA) unwinding activity of a helicase to generate single-stranded templates for primer annealing and extension by a strand-displacing DNA polymerase. Higher dsDNA unwinding activity of the helicase can promote more template-primer binding and contribute to higher amplification efficiency and a faster reaction. Thermophilic Helicase-Dependent Amplification (tHDA) utilizes a thermostable UvrD helicase (TteUvrD) to amplify selectively target sequences at 60-65° C., which shows improved amplification sensitivity without the need for the MutL accessory proteins. This study was designed to evaluate dsDNA unwinding efficiency of tHDA system using a microfluidic device, specifically LabChip® GX Touch™ Nucleic Acid Analyzer system. While such a device was employed in this instance, other devices, systems, and analytical methodologies may be implemented.

Two different pre-annealed duplexes were formed and the unwinding efficiency of tHDA system was analyzed. Annealing primer_80 and Target_80 provides a blunt-end, pre-annealed duplex product, whereas annealing Primer_80 and Target_110 provides a 3'-tailed end, pre-annealed duplex product. Primers were internally labeled with a fluorophore prior to forming the duplex. Oligos were obtained from either IDT or Eurofin. Sequences of the target strand and primer are shown in Table 1.

TABLE 1

| Oligonucleotide sequences. | | |
| --- | --- | --- |
| Name | Type | Sequence (5'-3') |
| Target_80 (80mer) | ssDNA | CACAATCAAATGACACAGACTGTGTGTAGT GTGAAAGTTAATCGAACTGTTGGAATCTGC ACGTTCAGCATAGCTTGCAT (SEQ ID NO: 1) |
| Target_110 (110mer) | ssDNA | CACAATCAAATGACACAGACTGTGTGTAGT GTGAAAGTTAATCGAACTGTTGGAATCTGC ACGTTCAGCATAGCTTGCATACAAGAGCGC TCATGAGACAATAACACTGA (SEQ ID NO: 2) |
| Primer_80 (20mer) | ssDNA with internally labeled CY5 | ATGCAAGCTA/iCy5/TGCTGAACGT (SEQ ID NO: 3) |

Pre-annealed duplex was prepared by mixing primer and target strand in 1× Anneal Buffer II from a tHDA Kit (IsoAmp® II Universal tHDA Kit, catalog #H0110S) in an approximately 1:1 molar ratio. The final duplex concentration was 250 nM. The annealing mixture was heated at 95° C. for 2 min, and then slowly cooled to 25° C. with a ramp rate of 0.1° C. per second.

Isothermal amplification reaction mixture was prepared by mixing the following components in 1× Annealing Buffer II (total volume of 20 μL): 4 mM $MgSO_4$, 40 mM NaCl, 1.4 μL of IsoAmp® dNTP Solution, 1.4 μL of IsoAmp® Enzyme Mix, and various amounts of pre-annealed duplex and primer.

Four conditions of pre-annealed duplex and primer mixtures were evaluated: 100 nM pre-annealed duplex only (A5, B4); 50 nM pre-annealed duplex+50 nM primer (Primer_80) (A4, B3); 20 nM pre-annealed duplex+80 nM primer (Primer_80) (A3, B2); and 100 nM primer (Primer_80) only (A1, A2, B1).

The IsoAmp® Enzyme Mix (condition A3-A5) was replaced with Bst DNA Polymerase Large Fragment (B2-B4) to test the baseline polymerase extension activity from Bst DNA Polymerase without duplex unwinding by helicase. In addition, a reaction mixture was prepared with 100 nM primer (Primer_80) without enzyme and pre-annealed templates to test the impact of enzymes and buffer on the migration of the primer (A2). Each reaction mixture was incubated at 65° C. for 20 minutes and then inactivated at 95° C. for 5 minutes. Products were analyzed using a LabChip® GX Touch™ instrument (PerkinElmer, part #CLS137031) with PerkinElmer's Fluorescence Fragment Analysis Evaluation kit. Data analysis was performed using LabChip® GX Reviewer software (perkinelmer.com/lab-products-and-services/resources/labchip-and-optimizer-software-downloads.html).

Figure 3A:
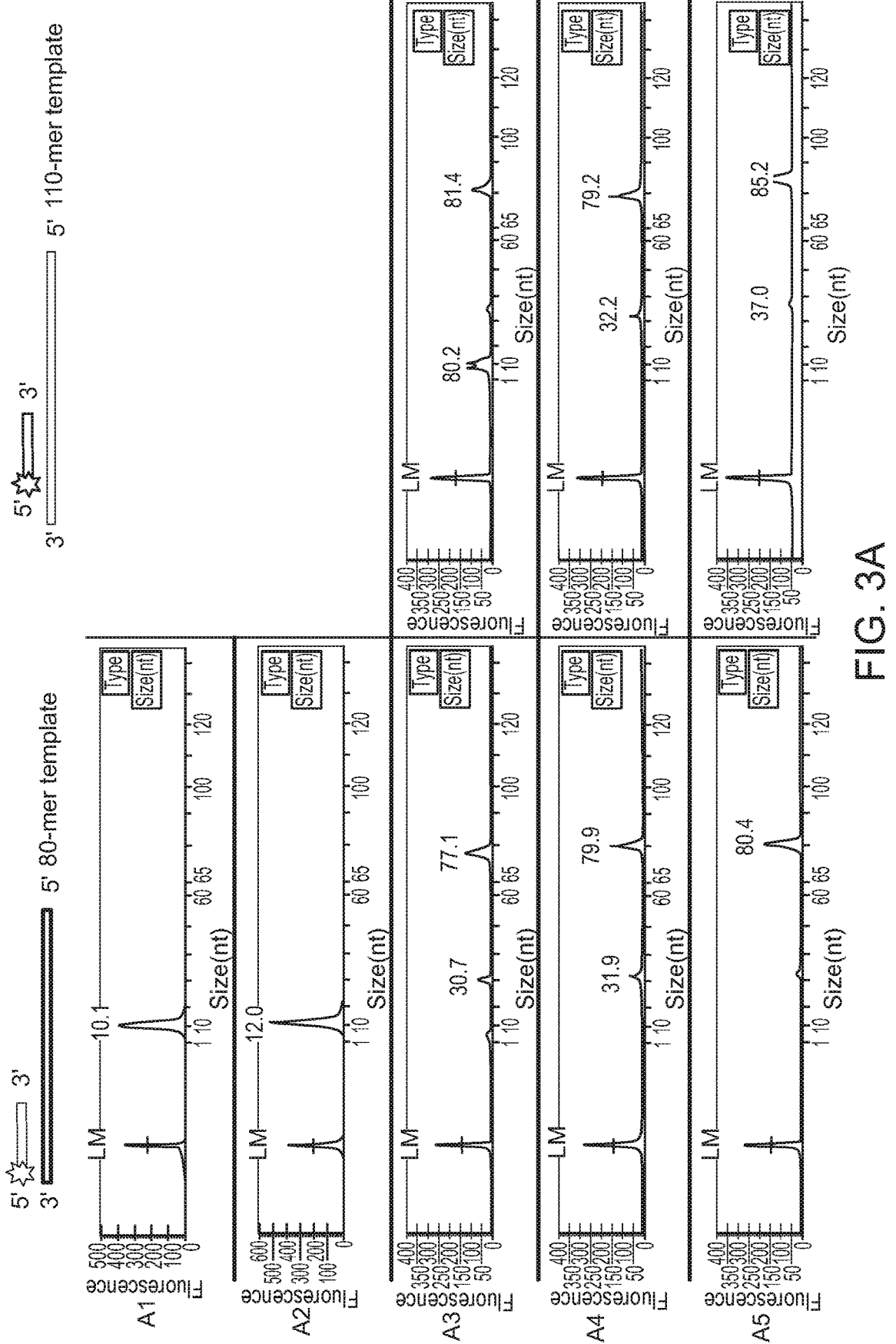
FIGS. 3A-3B are images of electropherograms from analysis of tHDA unwinding efficiency using Design 1. Schematic diagrams of the pre-annealed duplex structures used in the reactions are shown above each panel. Left panel: reaction mixtures included pre-annealed duplexes with a blunt end (at the 3'-end of the template) and a 5'-tailed end. Right panel: reaction mixtures included pre-annealed duplexes with a 5'-tailed end and a 3'-tailed end. Reaction mixtures included different ratios of pre-annealed duplexes and fluorescently-labeled primers (see Table 2). Reaction mixtures included tHDA (FIG. 3A) or BstLF (FIG. 3B).
Figure 3B:
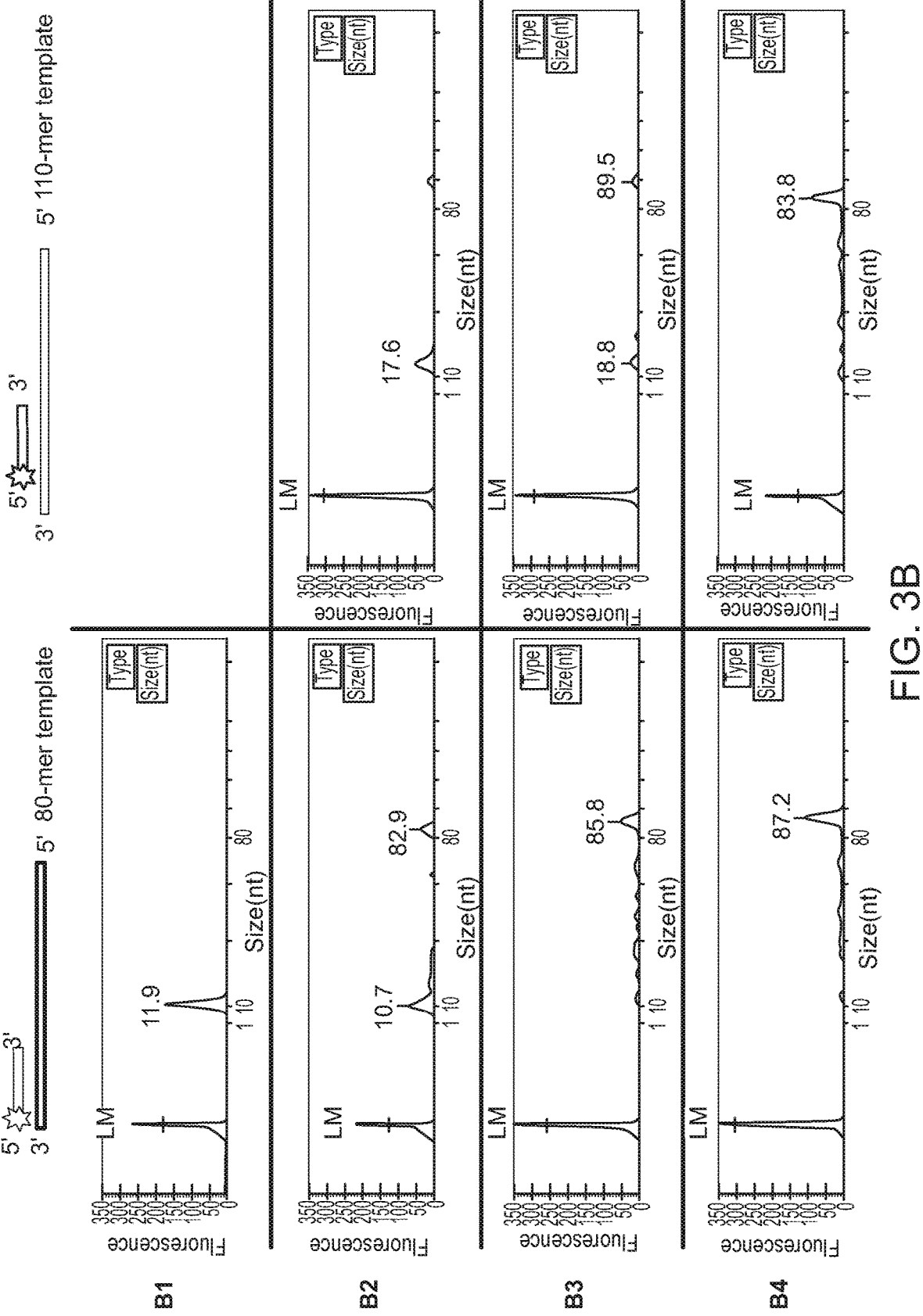

As shown in FIGS. 3A-3B and Table 2, the initial primer size was about 10-12 nt (observed size), and the fully extended product size was about 77 nt (observed size). Partial extended products between 15 to 77 nt were detected. The results are summarized as follows:

A1, B1: No duplex control, the fully extended product is 0%.

A2: No enzyme control, the fully extended product is 0%.

A3 and B2: No extra primer control, the fully extended product is around 100%.

A4-A5: The duplex with blunt ends has higher unwinding efficiency (more fully extended product) than that without blunt ends for all evaluated primer:duplex ratios.

B3-B4: The duplex with blunt ends has higher unwinding efficiency (more fully extended product) than that without blend ends for all evaluated primer:duplex ratios.

B2-B4: the duplex can be unwound for polymerase extension in the absence of an unwinding enzyme and in the presence of BstLF DNA polymerase. This might be due to "thermal breathing" of duplex DNA or to denaturation of duplex DNA at the reaction temperature (65° C.). Since the duplex includes a 20 mer, it is a short double-stranded nucleic acid, which can be more sensitive to elevated temperatures.

TABLE 2

Summary of experiment details and results.

| | | Experiment Details | | | Fully extended product percentage[a] | |
| | | | | | Pre-annealed | Pre-annealed |
| Condition | Enzyme | Pre-annealed template | Primers | Primer:Duplex ratio | template: Blunt end | Template: 3'-tailed end |
| --- | --- | --- | --- | --- | --- | --- |
| A1 | tHDA Enzyme Mix | 0 nM | 100 nM | 1:0 | 0% | 0% |
| A2* | Replaced enzyme with water | 0 nM | 100 nM | 1:1 | 0% | Not Determined |
| A3 | tHDA Enzyme Mix | 20 nM | 80 nM | 4:1 | 81.31% | 25.53% |
| A4 | tHDA Enzyme Mix | 50 nM | 50 nM | 1:1 | 86.86% | 86.71% |
| A5 | tHDA Enzyme Mix | 100 nM | 0 nM | 0:1 | 100% | 91.01% |
| B1 | BstLF | 0 nM | 100 nM | 1:0 | 0% | 0% |
| B2 | BstLF | 20 nM | 80 nM | 4:1 | 23.82% | 0% |
| B3 | BstLF | 50 nM | 50 nM | 1:1 | 100% | 38.29% |
| B4 | BstLF | 100 nM | 0 nM | 0:1 | 100% | 100% |

*Only tested with blunt-end template.
[a]Total peak area includes all peak size area (initial primer, partial extended and fully extended products). Fully extended peak percentage is calculated as fully extended peak area divide by total peak area.

Taken together, the experimental results described herein demonstrate that unwinding efficiency of a DNA helicase under isothermal amplification conditions can be detected using a fluorescently-labeled primer that is added in excess in the reaction mixture and that is used to form a pre-annealed duplex including a target strand and the fluorescently-labeled primer (Design 1). In some non-limiting instances, the extended products (either partial or full) can be an indicator of the success of the multi-enzyme synchronization events.

Example 2: Detecting Unwinding of a Double Stranded Nucleic Acid by a DNA Helicase Using a Fluorescently-Labeled Primer (Design 2)

This Example describes detecting unwinding of double stranded nucleic acid by a DNA helicase using a short fluorescently-labeled primer that is added in the reaction mixture and a pre-annealed duplex in which one of the strands is fluorescently-labeled (Design 2). Oligonucleotide sequences used in this study are shown in Table 3.

TABLE 3

Oligonucleotide sequences.

| Name | Type | Sequence (5'-3') | Study |
| --- | --- | --- | --- |
| Target_110 (110mer) | ssDNA | CACAATCAAATGACACAGACTG TGTGTAGTGTGAAAGTTAATCG AACTGTTGGAATCTGCACGTTC AGCATAGCTTGCATACAAGAGC GCTCATGAGACAATAACACTGA (SEQ ID NO: 2) | tHDA/ RPA |
| Primer_80 (20mer) | ssDNA with intern-ally labeled CY5 | ATGCAAGCTA/iCy5/ TGCTGAACGT (SEQ ID NO: 3) | tHDA |
| Primer_80_v2 (35mer) | ssDNA with intern-ally labeled CY5 | ATGCAAGCTA/iCy5/TGCTGA ACGTGCAGATTCCAACAGT (SEQ ID NO: 4) | RPA |

TABLE 3-continued

Oligonucleotide sequences.

| Name | Type | Sequence (5'-3') | Study |
| --- | --- | --- | --- |
| Primer_110 | ssDNA with 5'-labeled CY5 | /5Cy5/TCAGTGTTATTGTCTC ATGA (SEQ ID NO: 5) | tHDA/ RPA |

This study was designed to evaluate dsDNA unwinding efficiency of tHDA system using a microfluidic device, specifically LabChip® GX Touch™ Nucleic Acid Analyzer system.

A 110 mer pre-annealed duplex was first prepared by a polymerase extension reaction using 2× Phire Hot Start II PCR Master (Thermofisher, catalog #F125S) with 3 μM primer (Primer_110) and 2.5 μM target strand (Target_110 mer) in a 20 μL reaction under the following thermal cycler program: 98° C./30 sec, 30 cycles (98° C./5 sec, 55° C./5 sec, 72° C./10 sec), 72° C./1 min following the user manual. The polymerase extension product was tested on LabChip® GX Touch™ Nucleic Acid Analyzer (PerkinElmer, catalog #CLS137031). Slight excess of primer was used to ensure there is no free complement strand (110 nt) in the reaction product. Otherwise, Primer_80 in the isothermal amplification reaction can bind to the free complement strand to generate short fragments (80 nt), thereby creating false positive fragments.

Figure 4:
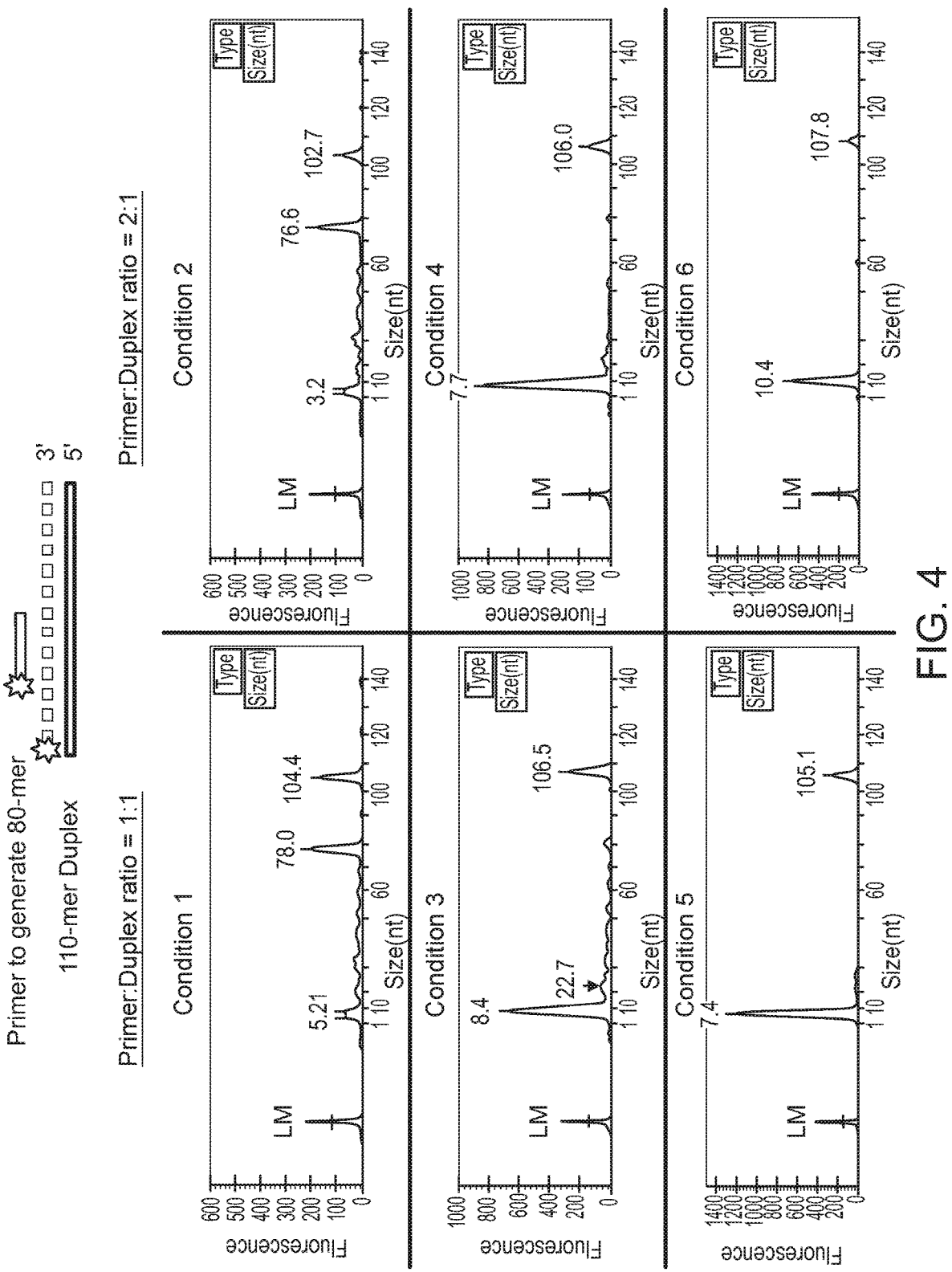
FIG. 4 are images of electropherograms from analysis of tHDA unwinding efficiency using Design 2. Left panel: primer-to-duplex ratio is 1:1. Right panel: primer-to-duplex ratio is 2:1.

The tHDA-based isothermal amplification reaction was conducted in a 20 μL reaction mixture with IsoAmp® II Universal tHDA Kit (NEB, catalog #H0110S) by mixing 4 mM MgSO$_4$, 40 mM NaCl, 1.4 μL of IsoAmp® dNTP solution, and 1.4 μL of IsoAmp® Enzyme Mix with two different primer/duplex preparations: 300 nM primer (Primer_80) and 300 nM 110 mer duplex; and 300 nM primer (Primer_80) and 150 nM duplex. The reaction mixture was incubated at 65° C. for 20 minutes and then inactivated at 95° C. for 5 minutes. IsoAmp® Enzyme Mix was substituted with water as negative control, and Bst DNA Polymerase Large Fragment (BstLF) (NEB, catalog #M0275S) was used as the polymerase control. Products were analyzed using a LabChip® GX Touch™ instrument (PerkinElmer, part #CLS137031) with PerkinElmer's Fluorescence Fragment Analysis Evaluation kit. Data analysis was performed using LabChip® GX Reviewer software (perkinelmer.com/lab-products-and-services/resources/labchip-and-optimizer-software-downloads.html).

tHDA unwinds dsDNA duplex with higher efficiency and leads to more primer extension products compared to BstLF. As shown in FIG. 4, two peaks are detected when the tHDA reaction system does not contain enzymes (condition 5, 6): the initial primer size is observed around 12 nt, and the 110 nt fragment of dsDNA duplex is observed around 105 nt. With tHDA enzymes present in the reaction system, the extended product (80 nt) from dsDNA unwinding event can be detected around 78 nt. When primer-to-duplex ratio is 1:1 (condition 1), the extended fragment is around 50% of total fragments (extended fragments and original duplex fragments), which indicates that most of the 300 nM duplex templates are unwound and that most of the 300 nM primers can be annealed to the target strand and extended to 80 nt. When primer-to-duplex ratio is 2:1 (condition 2), the extended fragment percentage increases to 65% indicating that more duplex structures (either from the initial templates or extended products) can be unwound and then annealed/extended with additional primers.

Comparatively, when only BstLF is present in the reaction system (condition 3, 4), the extended product (~80 nt peak) is not visible under both conditions. There is no efficient unwinding event or "thermal breathing" event for this duplex structure which is 110 bp with 41.8% GC and Tm (melting temperature) higher than 70° C. The double-stands with longer length are less impacted by high temperature comparing to double-strands with shorter length used in Design 1.

A summary of experimental details and results is provided in Table 4.

TABLE 4

Summary of experiment details and results.

| Condition | Enzyme | Pre-annealed duplex | Primers | Primer:duplex ratio | Short Fragment (extended product) percentage[a] |
|---|---|---|---|---|---|
| 1 | tHDA | 300 nM | 300 nM | 1:1 | 50% |
| 2 | tHDA | 150 nM | 300 nM | 2:1 | 65% |
| 3 | BstLF | 300 nM | 300 nM | 1:1 | 0% |
| 4 | BstLF | 150 nM | 300 nM | 2:1 | 0% |
| 5 | Water | 300 nM | 300 nM | 1:1 | 0% |
| 6 | Water | 150 nM | 300 nM | 2:1 | 0% |

[a]Total peak area includes initial 110-mer peak area and extended product 80-mer peak area. Extended peak percentage is calculated as extended peak area divided by total peak area.

Taken together, these data demonstrate that tHDA enzyme mix can unwind blunt-end dsDNA duplex efficiently and synchronize duplex unwinding, primer binding, and polymerase extension in just 20 minutes at defined tHDA isothermal amplification conditions in certain non-limiting instances. In further non-limiting instances, this design may be less impacted by "thermal breathing" or the effects related to heat denaturation. Therefore, such a design (or modified forms thereof) may be applicable for isothermal amplification unwinding efficiency characterization at broad temperature ranges, including at elevated temperatures, such as more than about 45° C.

Example 3: Detection of Duplex Strand Exchange Efficiency During Recombinase Polymerase Amplification (RPA)

This Example describes detection of strand exchange during recombinase polymerase amplification (RPA) using a short fluorescently-labeled primer that is added in the reaction mixture and a pre-annealed duplex in which one of the strands is fluorescently-labeled (Design 2). Oligonucleotide sequences used in this study are shown in Table 3.

The RPA process operates at 37-42° C. and starts when a recombinase protein uvsX binds to primers forming a recombinase-primer complex which then initiates a strand exchange/invasion process to open the duplex. Primers of 30-35 nucleotides in length be used for in RPA reactions, although primers as short as 18 nt can work. This study was designed to evaluate the strand exchange/invasion efficiency of the RPA system with two different primer designs using PerkinElmer's LabChip® GX Touch™ Nucleic Acid Analyzer system.

Pre-annealed duplexes were formed as described in Example 2. RPA-based isothermal amplification reactions were conducted in a 50 μL reaction mixture with Twist-Amp® Liquid Basic Kit (TwistDx, catalog #TALQAS01) by mixing 25 μL of 2× Reaction Buffer, 5 μL of 10× Basic E-Mix, 14 mM MgOAc, 1.8 mM (Total) dNTP, and 2.5 μL of 20× Core Reaction Mix with two different primer/duplex preparations: 300 nM primer (Primer_80_v2, 35 nt) and 300 nM 110 mer duplex; and 300 nM primer (Primer_80_v2) and 150 nM 110 mer duplex. The reaction mixture was incubated at 37° C. for 20 minutes and then inactivated at 95° C. for 5 minutes. As a control, 20× Core Reaction Mix (RPA enzyme mix) was substituted with water as negative control, and Bst DNA Polymerase Large Fragment as polymerase control because it can have some activity at 37° C. In addition, the primer length preference of RPA-based amplification was tested by replacing Primer_80_v2 with a 20 nt primer (Primer_80) in the reaction mixture.

After isothermal amplification, nucleic acid purification was performed using ZR-96 Oligo Clean & Concentrator kit (ZYMO RESEARCH, catalog #D4062). 100 μL of oligo binding buffer was first added to 50 μL of amplification products, which were then mixed with 400 μL of ethanol (Sigma, catalog #459828-1L) and transferred to the Zymo-Spin™ I-96 plate mounted on a collection plate. After a 5-minute centrifugation at 2500×g room temperature, the column was washed once with 750 μL of DNA wash buffer and centrifuged twice at 2500×g room temperature for 5 minutes to ensure complete removal of the wash buffer. Then, the plate was transferred onto an elution plate, and 25 μL of water was added directly to the matrix of each well. In the end, the plate was centrifuged at 2500×g room temperature for 5 minutes to collect the elute. 3 μL of the products were analyzed by PerkinElmer's Fluorescence Fragment Analysis Evaluation kit following the evaluation user guide. Data analysis was performed using LabChip® GX Reviewer software (perkinelmer.com/lab-products-and-services/resources/labchip-and-optimizer-software-downloads.html).

Figure 5:
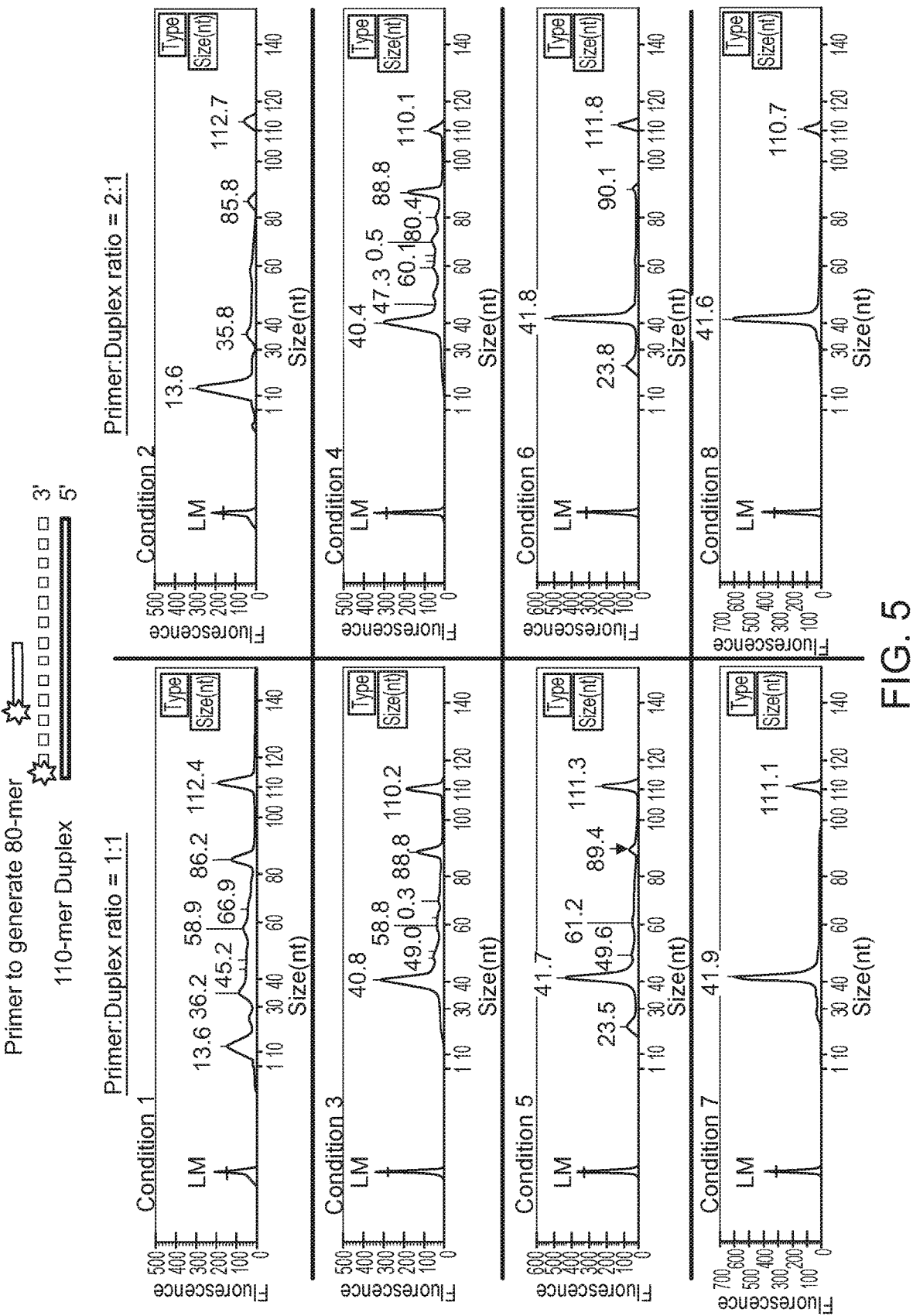
FIG. 5 are images of electropherograms from analysis of duplex strand exchange efficiency of RPA using Design 2. Left panel: primer-to-duplex ratio is 1:1. Right panel: primer-to-duplex ratio is 2:1.

The RPA enzyme mix opens dsDNA duplex and extends the primer using the unwound duplex template with higher efficiency for longer primers, as compared to the polymerase control. As shown in FIG. 5, two peaks can mainly be detected when no enzyme is present within the RPA system: primers (observed at 41 nt for 35 nt primer in conditions 7 and 8, and observed at 13 nt for 20 nt primer (data not shown)) and 110 nt initial fragments from dsDNA duplex (observed at 111 nt). With RPA enzyme mix, the extended product 80 nt can be detected at around 87 nt. However, the extended-to-initial fragment ratio is only 0.7 under the 20 nt primer condition and with multiple small fragments less than 80 nt. Under the 35 nt primer condition, the extended-to-initial fragment ratio is 0.8 when primer-to-duplex ratio is 1:1, and increases to 2.7 when primer-to-duplex ratio is 2:1. As a comparison, when BstLF polymerase is used without the recombinase mixture, the amount of polymerase extension product decreases significantly with an extended-to-initial fragment ratio of 0.3, which does not increase even when primer-to-duplex ratio increases to 2:1. A summary of experimental details and results is provided in Table 5.

TABLE 5

Summary of experiment details and results.

| Condition | Primer | Enzyme | Pre-annealed duplex | Primers | Primer:duplex ratio | Short Fragment (extended product) percentage[a] | Extended-to-initial fragment ratio |
|---|---|---|---|---|---|---|---|
| 1 | 20 nt | RPA | 300 nM | 300 nM | 1:1 | 37% | 0.7 |
| 2 | | RPA | 150 nM | 300 nM | 2:1 | 37% | 0.7 |
| 3 | 35 nt | RPA | 300 nM | 300 nM | 1:1 | 42% | 0.8 |
| 4 | | RPA | 150 nM | 300 nM | 2:1 | 71% | 2.7 |
| 5 | | Bst LF | 300 nM | 300 nM | 1:1 | 22% | 0.3 |
| 6 | | Bst LF | 150 nM | 300 nM | 2:1 | 22% | 0.3 |
| 7 | | Water | 300 nM | 300 nM | 1:1 | 0% | 0 |
| 8 | | Water | 150 nM | 300 nM | 2:1 | 0% | 0 |

[a]Total peak area includes initial 110-mer peak area and extended product 80-mer peak area. Extended peak percentage is calculated as extended peak area divided by total peak area.

These results suggest that with the strand exchange activity of the RPA enzyme mixture provides higher amplification efficiency compared to the BstLF polymerase, and that the RPA system has a higher strand exchange efficiency with longer primers (35 nt) compared to short primers (20 nt). These results also demonstrate that amplification, in certain non-limiting instances, can occur in just 20 minutes under the RPA isothermal amplification conditions described herein.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting unwinding or strand exchange of a double stranded nucleic acid, the method comprising:
   providing a sample comprising a pre-annealed duplex, wherein the pre-annealed duplex comprises a target nucleic acid and a synthetic nucleic acid comprising an optional first detectable label; a primer comprising a second detectable label; an amplifying enzyme for amplifying nucleic acids; and an unwinding enzyme for unwinding or strand exchange double stranded nucleic acids;
   incubating the sample under an isothermal amplification condition and for a time sufficient for nucleic acid amplification; and
   detecting the second detectable label and, optionally, the first detectable label, if present,
   wherein a ratio of the primer to the pre-annealed duplex is from 1:1 to 50:1.

2. The method of claim 1, wherein the synthetic nucleic acid comprises an initial primer, and wherein the initial primer comprises the first detectable label.

3. The method of claim 2, wherein said incubating further comprises:
   extending the initial primer, thereby providing an extension product comprising the first detectable label;
   unwinding the extension product;
   annealing the primer comprising the second detectable label to a portion of the target nucleic acid; and
   extending the primer, thereby providing a further extension product comprising the second detectable label.

4. The method of claim 1, wherein the synthetic nucleic acid comprises an extension product of an initial primer, and wherein the initial primer comprises the first detectable label.

5. The method of claim 1, wherein the synthetic nucleic acid comprises an elongated nucleic acid comprising about 20 or more nucleotides.

6. The method of claim 5, wherein the elongated nucleic acid comprises the first detectable label.

7. The method of claim 1, wherein said incubating further comprises:
   unwinding the duplex;
   annealing the primer comprising the second detectable label to a portion of the target nucleic acid; and
   extending the primer, thereby providing an extension product comprising the second detectable label.

8. The method of claim 1, further comprising, prior to said providing:
   annealing the target nucleic acid and the synthetic nucleic acid, thereby forming the pre-annealed duplex; and
   optionally cooling the pre-annealed duplex.

9. The method of claim 1, further comprising, prior to said providing:
   annealing the target nucleic acid and the synthetic nucleic acid, wherein the synthetic nucleic acid is configured to be an initial primer; and
   extending the initial primer under a polymerase primer extension condition, thereby forming the pre-annealed duplex.

10. The method of claim 1, further comprising, after said incubating:
   inactivating the sample using thermal inactivation and/or chemical inactivation.

11. The method of claim 1, further comprising prior to said detecting:
   purifying the sample to remove one or more chemical or biological components.

12. The method of claim 1, wherein the synthetic nucleic acid and the primer comprises the same nucleic acid sequence.

13. The method of claim 1, wherein the synthetic nucleic acid is shorter than or the same length as the primer.

14. The method of claim 1, wherein the synthetic nucleic acid is longer than the primer.

15. The method of claim 1, wherein the synthetic nucleic acid and the primer has, independently, a length of about 5 to 100 nucleotides.

16. The method of claim 1, wherein the pre-annealed duplex comprises a 3'-tailed end and/or a 5'-tailed end.

17. The method of claim 1, wherein the pre-annealed duplex comprises at least one blunt end.

18. The method of claim 1, wherein the pre-annealed duplex has a length of about 15 to 500 base pairs.

19. The method of claim 1, wherein the first and second detectable labels are same or different.

20. The method of claim 19, wherein the first and second detectable labels are, independently, provided at a 5'-end or internally.

21. The method of claim 19, wherein the synthetic nucleic acid comprises a plurality of first detectable labels, and/or wherein the primer comprises a plurality of second detectable labels.

22. The method of claim 19, wherein the first and second detectable labels are selected from the group consisting of a fluorescent label, a radioactive label, a chemiluminescent label, or a dye.

23. The method of claim 1, wherein the sample further comprises 3'-amino-2',3'-dideoxyribonucleotide 5'-triphosphates (nNTPs), a divalent ion, a denaturant, a buffer, and/or a salt.

24. The method of claim 1, wherein the amplifying enzyme and/or the unwinding enzyme is selected from the group consisting of a helicase, a recombinase, a polymerase, a reverse transcriptase, a thermophilic form thereof, a thermostable form thereof, and a recombinant form thereof.

26

25. The methods of claim 1, wherein the isothermal amplification condition comprises a temperature of about 20 to 75° C.

26. The method of claim 1, wherein said detecting comprises electrophoresis analysis, optionally on a microfluidic device.

27. The method of claim 26, wherein the electrophoresis analysis comprises analysis of fragment size of an amplicon comprising the second detectable label.

28. The method of claim 27, wherein the electrophoresis analysis further comprises comparing the fragment size of the amplicon to a labeled size standard.

* * * * *